(12) United States Patent
Pichette et al.

(10) Patent No.: US 9,499,509 B2
(45) Date of Patent: Nov. 22, 2016

(54) DIHYDROCHALCONE DERIVATIVES AND THEIR USE AS ANTIBIOTIC AGENTS

(71) Applicant: UNIVERSITÉ DU QUÉBEC À CHICOUTIMI, Chicoutimi (CA)

(72) Inventors: André Pichette, Chicoutimi (CA); Jean Legault, La Baie (CA); François Simard, Jonquière (CA)

(73) Assignee: UNIVERSITE DU QUEBEC A CHICOUTIMI, Chicoutimi (CA)

( * ) Notice: Subject to any disclaimer, the term of this patent is extended or adjusted under 35 U.S.C. 154(b) by 0 days.

(21) Appl. No.: 14/425,147

(22) PCT Filed: Aug. 28, 2013

(86) PCT No.: PCT/CA2013/050665
§ 371 (c)(1),
(2) Date: Mar. 2, 2015

(87) PCT Pub. No.: WO2014/032183
PCT Pub. Date: Mar. 6, 2014

(65) Prior Publication Data
US 2015/0210663 A1    Jul. 30, 2015

Related U.S. Application Data

(60) Provisional application No. 61/694,480, filed on Aug. 29, 2012, provisional application No. 61/807,473, filed on Apr. 2, 2013.

(51) Int. Cl.
*A61K 31/35* (2006.01)
*C07D 311/62* (2006.01)
(Continued)

(52) U.S. Cl.
CPC .............. *C07D 311/62* (2013.01); *A61K 36/76* (2013.01); *C07C 49/835* (2013.01); *C07C 49/84* (2013.01); *C07D 311/60* (2013.01); *A61K 2236/00* (2013.01)

(58) Field of Classification Search
CPC . C07D 311/62; C07D 311/60; C07C 49/835; C07C 49/84; A61K 31/35
USPC ........................................................ 514/456
See application file for complete search history.

(56) References Cited

U.S. PATENT DOCUMENTS 5,434,183 A    7/1995    Larsson-Backstrom

OTHER PUBLICATIONS

Conserva et al, The Chemistry of Brazilian Myristicaceae. Part 32. Iryantherins, lignoflavonoids of novel structural types from the Myristicaceae, Phytochemistry, 1990, 29(12), p. 3911-3918.*

(Continued)

*Primary Examiner* — T. Victor Oh
(74) *Attorney, Agent, or Firm* — Julie Gauvreau

(57) ABSTRACT

A compound of formula (I) as well as pharmaceutical compositions comprising same is provided. An extract of a plant belonging to a species of *Populus*, the extract comprising this compound is also provided. These can be used as antibacterial for treating bacterial infection.

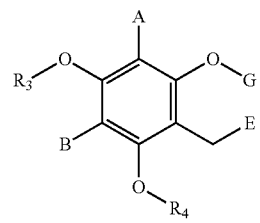

29 Claims, 19 Drawing Sheets

(51) Int. Cl.
    *A61K 36/76*     (2006.01)
    *C07D 311/60*     (2006.01)
    *C07C 49/84*     (2006.01)
    *C07C 49/835*     (2006.01)

(56) References Cited

OTHER PUBLICATIONS

Ansel et. al., Pharmaceutical Dosage Forms and Drug Delivery Systems (6th Ed. 1995) p. 196. (excerpt).
Azad Eh Eftekhari, "Chemical and Biological Study on Constituents of Populus Tremuloides Buds" Universite Du Quebec, Dec. 2009.
Bingham al, "Over one hundred solvates of sulfathiazole" Chem. Commun., 603-604 (2001).
Caira et al, "Preparation and Crystal Characterization of a Polymorph, a Monohydrate, and an Ethyl Acetate Solvate of the Antifungal Fluconazole" J. Pharmaceutical Sci., 93(3), 601-611 (2004).
Hsieh et al., "Current Prodrug Design for Drug Discovery" Curr. Pharm. Des., 15 (19), pp. 2236-2250 (2009).
International Search Report and Written Opinion in PCT/CA2013/050665 to Université du Québec à Chicoutimi, mailed Dec. 5, 2013.
Isidorov V. et al. "GC-MS Ananlysis of Compounds Extracted from Buds of Populus balsamifera and Populus nigra" Z. Naturfrosch. vol. 58c, pp. 355-360, 2003.
Jarkko Rautio et al., "Prodrugs: design and clinical applications", Nat. Rev. Drug Discov., 7, pp. 255-270 (2008).
Krogsgaard-Larsen et. al., Textbook of Drug Design and Development (4th Ed. 2010) at pp. 135-149.
Pichette A. et al. "Cytotoxic phenolic compounds in leaef buds of Populus tremuloides" Can. J. Chem. vol. 88, pp. 104-110, 2010.
Remington's Pharmaceutical Sciences, 16th Ed., 1980, A. Oslo Ed., Easton, Pa., Chapter 83, pages (excerpt).
Van Tonder et al, "Preparation and Physicochemical Characterization of 5 Niclosamide Solvates and 1 Hemisolvate" AAPS Pharm Sci Tech., 5(1), article 12 (2004).
Ansel et. al., Pharmaceutical Dosage Forms and Drug Delivery Systems (10th Ed. 2014) pp. 128-129.
Extended European Search Report in EP13834219.1 to Université du Québec à Chicoutimi, mailed Feb. 9, 2016.

\* cited by examiner

DIHYDROCHALCONE DERIVATIVES AND THEIR USE AS ANTIBIOTIC AGENTS

CROSS REFERENCE TO RELATED APPLICATIONS

This application is a National Entry Application of PCT application Serial No. PCT/CA2013/050665* filed on Aug. 28, 2013 and published in English under PCT Article 21(2), which itself claims benefit of U.S. provisional application Ser. No. 61/694,480 filed on Aug. 29, 2012 and Ser. No. 61/807,473, filed on Apr. 2, 2013. All documents above are incorporated herein in their entirety by reference.

FIELD OF THE INVENTION

The present invention relates to dihydrochalcone derivatives and their use as antibiotic agents.

BACKGROUND OF THE INVENTION

An antibiotic agent is a drug that kills bacteria or slows their growth. Antibiotics are relatively harmless to the host, and therefore can be used to treat infections.

Antibiotics can be administered in a variety of ways, including orally, intravenously and topically.

There are relatively few classes of antibiotics currently available to treat bacterial infections. Several of the known antibiotics have significant side effects, such as dangerous allergic reactions or inconvenient gastrointestinal disturbances (see Table 1).

TABLE 1

Existing classes of antibiotics and their known side effects.

| Class | Antibiotic Generic Name | Known Side Effects |
| --- | --- | --- |
| Aminoglycosides | Amikacin; Gentamicin; Kanamycin; Neomycin; Netilmicin; Streptomycin; Tobramycin | Hearing loss Vertigo Kidney damage |
| Carbacephem | Loracarbef | |
| Carbapenems | Ertapenem; Imipenem/Cilastatin; Meropenem | |
| Cephalosporins (First, second, third and fourth generations) | Cefadroxil; Cefazolin; Cephalexin; Cefaclor; Cefamandole; CefoxitinCefprozil; Cefuroxime; Cefixime; Cefdinir; Cefditoren; Cefoperazone; Cefotaxime; Cefpodoxime; Ceftazidime; Ceftibuten; Ceftizoxime; Ceftriaxone; Cefepime; | Gastrointestinal upset and diarrhea Nausea (if alcohol taken concurrently) Allergic reactions |
| Glycopeptides | Vancomycin; | |
| Macrolides | Azithromycin; Clarithromycin; Dirithromycin; Erythromycin; Roxithromycin; Troleandomycin | |
| Monobactam | Aztreonam; | |
| Penicillins | Amoxicillin; Ampicillin; Azlocillin; Carbenicillin; Cloxacillin; Dicloxacillin; Flucloxacillin; Mezlocillin; Nafcillin; Penicillin; Piperacillin; Ticarcillin | Gastrointestinal upset and diarrhea Allergy with serious anaphylactic reactions Brain and kidney damage |
| Polypeptides | Bacitracin; Colistin; Polymyxin; B | Kidney and nerve damage (when given by injection) |
| Quinolones | Ciprofloxacin; Enoxacin; Gatifloxacin; Levofloxacin; Lomefloxacin; Moxifloxacin; Norfloxacin; Ofloxacin; Trovafloxacin; | Nausea |
| Sulfonamides | Mafenide; Prontosil (archaic); Sulfacetamide; Sulfamethizole; Sulfanilimide (archaic); Sulfasalazine; Sulfisoxazole; Trimethoprim; Trimethoprim-Sulfamethoxazole (Co-trimoxazole) (TMP-SMX) | Nausea, vomiting, and diarrhea Allergy (including skin rashes) Crystals in urine Kidney failure Decrease in white blood cell count Sensitivity to sunlight |
| Tetracyclines | Demeclocycline; Doxycycline; Minocycline; Oxytetracycline; Tetracycline | Gastrointestinal upset Sensitivity to sunlight Staining of teeth Potential toxicity to mother and fetus during pregnancy |
| Others | Chloramphenicol; Clindamycin; Ethambutol; Fosfomycin; Furazolidone; Isoniazid; Linezolid; Metronidazole; Nitrofurantoin; Platensimycin; Pyrazinamide; Guinupristin/Dalfopristin; Rifampin; Spectinomycin | |

All antibiotics have a certain delimited spectrum of action. This spectrum of action can sometimes be very narrow. For example, antibiotics activity can be limited to gram-positive or gram-negative bacteria.

In consequence, there are only a limited number of antibiotics that can be used for treating any given infection. Faced with this limited choice, physicians are sometimes forced to prescribe antibiotics having side effects.

There are also serious concerns about strains of bacteria developing antibiotic resistance making them untreatable by any available antibiotics. Indeed, one of the most frequent problems in hospital is the presence of bacteria resistant to the most common antibiotic agents. One such resistant strain of bacteria is methicillin-resistant *Staphylococcus aureus* (MRSA). MRSA is a bacterium responsible for difficult-to-treat infections in humans. It may also be referred to as multiple-resistant *Staphylococcus aureus* or oxacillin-resistant *Staphylococcus aureus* (ORSA). MRSA is a resistant variation of the common bacterium *Staphylococcus aureus*. It has evolved an ability to survive treatment with beta-lactam antibiotics, including penicillin, methicillin, and cephalosporins. MRSA is especially troublesome in hospital-associated (nosocomial) infections. In hospitals, patients with open wounds, invasive devices, and weakened immune systems are at greater risk for infection than the general public. Hospital staff that does not follow proper sanitary procedures may transfer bacteria from patient to patient. MRSA is now found worldwide. MRSA is often referred to in the press as a "superbug." In the past decade or so the number of MRSA infections in the United States has increased significantly. Some published figures suggest that MRSA infections are responsible for more deaths in the U.S. each year than AIDS. Vancomycin is the latest treatment now used for treating MRSA, but new strains of *Staphylococcus aureus* presenting a resistance to vancomycin (VRSA) are now appearing.

There is therefore a need for new chemical compounds having antibiotic properties. The present invention therefore aims to provide such compounds.

The present description refers to a number of documents, the content of which is herein incorporated by reference in their entirety.

SUMMARY OF THE INVENTION

In accordance with the present invention, there is provided

1. A compound of formula (I):

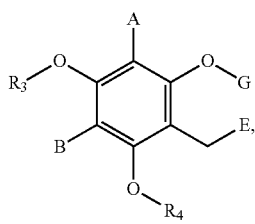

wherein:
one of A and B is H and the other is

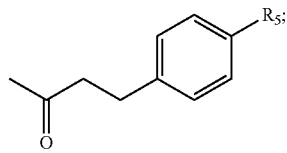

G is $R_2$ and E is

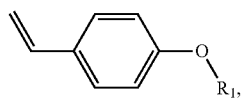

or

G and E are both carbon atoms, said carbon atoms being linked together by a single bond, G being substituted by

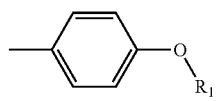

and E being substituted by $R_6$;

each of $R_1$, $R_2$, $R_3$, and $R_4$ independently being H or alkyl; and each of $R_5$ and $R_6$, independently being H, OH, alkyl, or alkoxy, or a salt, ester, or solvate thereof.

2. The compound of item 1, being of formula (1), (2) or (3):

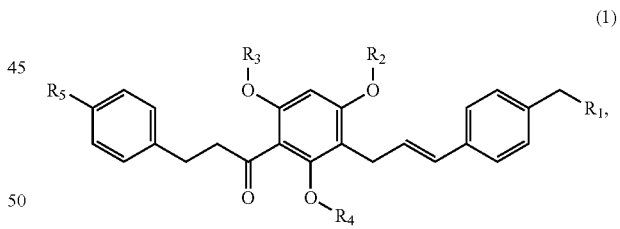

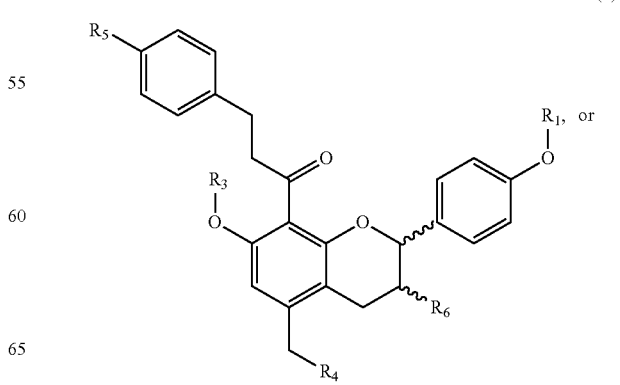

-continued

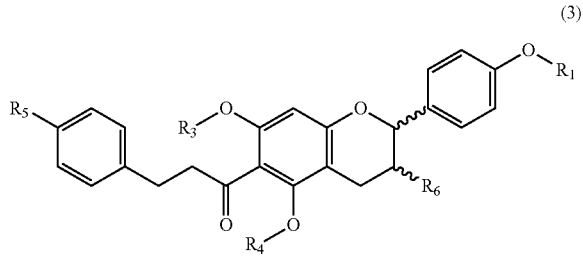

(3)

or a salt, ester or solvate thereof.

3. The compound of item 1 or 2, wherein $R_1$ is H.
4. The compound of any one of items 1 to 3, wherein $R_2$ is H or $CH_3$.
5. The compound of any one of items 1 to 4, wherein $R_3$ is H.
6. The compound of any one of items 1 to 5, wherein $R_4$ is H or —$CH_3$.
7. The compound of any one of items 1 to 6, wherein $R_5$ is H, —OH or —O—$CH_3$.
8. The compound of any one of items 1 to 7, wherein $R_6$ is H or —OH.
9. A compound of formula (1):

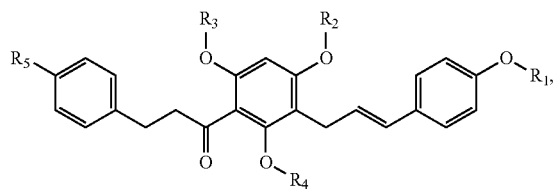

(1)

wherein:

| $R_1$ | $R_2$ | $R_3$ | $R_4$ | $R_5$ |
|---|---|---|---|---|
| H | $CH_3$ | H | H | OH; |
| H | H | H | H | —$OCH_3$; or |
| H | H | H | H | H, | or a salt, ester, or solvate thereof.

10. A compound of formula (2):

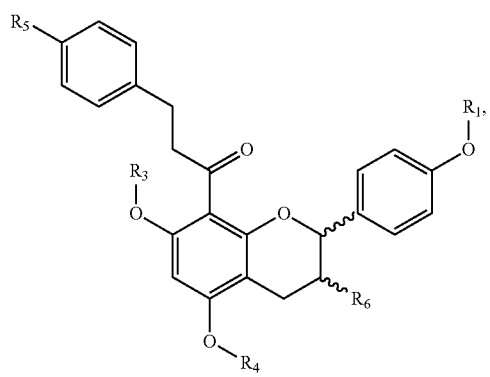

(2)

wherein:

| $R_1$ | $R_4$ | $R_3$ | $R_5$ | $R_6$ | Stereochemistry |
|---|---|---|---|---|---|
| H | H | H | H | H | Racemic; |
| H | H | H | H | H | 2S; |
| H | H | H | H | H | 2R; |
| H | H | H | —O—$CH_3$ | H | Racemic; |
| H | H | H | —O—$CH_3$ | H | 2S; |
| H | H | H | —O—$CH_3$ | H | 2R; |
| H | $CH_3$ | H | OH | H | Racemic; |
| H | $CH_3$ | H | OH | H | 2S; |
| H | $CH_3$ | H | OH | H | 2R; |
| H | H | H | H | OH | Racemic; |
| H | H | H | H | OH | 2S, 3S; |
| H | H | H | H | OH | 2S, 3R; |
| H | H | H | —O—$CH_3$ | OH | Racemic; |
| H | H | H | —O—$CH_3$ | OH | 2R, 3S; or |
| H | H | H | —O—$CH_3$ | OH | 2S, 3R, | or a salt, ester, or solvate thereof.

11. A compound of formula (3):

(3)

wherein:

| $R_1$ | $R_3$ | $R_4$ | $R_5$ | $R_6$ | Stereochemistry |
|---|---|---|---|---|---|
| H | H | H | H | OH | Racemic; |
| H | H | H | H | OH | 2R, 3S; or |
| H | H | H | H | OH | 2S, 3R, | or a salt, ester, or solvate thereof.

12. The compound of any one of items 1 to 11, wherein said compound is in free base form.
13. The compound of any one of items 1 to 11, wherein said compound is a pharmaceutically acceptable salt.
14. The compound of any one of items 1 to 11, wherein said compound is a pharmaceutically acceptable ester.
15. The compound of any one of items 1 to 11, wherein said compound is a pharmaceutically acceptable solvate.
16. The compound of item 15, wherein said solvate is an hydrate.
17. An extract of a plant belonging to a species of *Populus*, the extract comprising at least one compound of formula (I) as described above.
18. The extract of item 17, wherein the plant is *Populus balsamifera*.
19. The extract of item 18, being an extract of *Populus balsamifera* buds.
20. The extract of item 19, being an ethanolic extract, or a combination of several such extracts, in liquid form or dried form.
21. A methanolic extract of the dried ethanolic extract of item 20, said methanolic extract fraction having optionally been extracted with hexane one or more times, said methanolic extract being in liquid or dried form.
22. A diethyl ether extract of the methanolic extract of item 21, said diethyl ether extract having optionally been extracted with water one or more times, said diethyl ether extract being in liquid or dried form.

23. A fraction of the dried diethyl ether extract of item 22.

24. Use of (i) the compound of any one of items 1 to 11, or of (ii) a pharmaceutically acceptable salt, ester or solvate of (i), or of (iii) the extract of any one of items 17-22, or (iv) of the fraction of 23, in the preparation of a medicament.

25. The use of item 24, wherein said medicament is for treating a bacterial infection (e.g., a *Staphylococcus* such as *Staphylococcus aureus* (e.g., wild type or MRSA) or *Staphylococcus epidermidis*).

26. Use of (i) the compound of any one of items 1 to 11, or of (ii) a pharmaceutically acceptable salt, ester or solvate of (i) or of (iii) the extract of any one of items 17-22, or of (iv) the fraction of item 23, for treating a bacterial infection (e.g., a *Staphylococcus* such as *Staphylococcus aureus* (e.g., wild type or MRSA) or *Staphylococcus epidermidis*).

27. A pharmaceutical composition comprising (i) the compound of any one of items 1 to 11, or (ii) a pharmaceutically acceptable salt, ester or solvate of (i); or (iii) the extract of any one of items 17-22, or (iv) the fraction of item 23.

28. The pharmaceutical composition of item 27, further comprising a pharmaceutically acceptable carrier.

29. The compound, salt, ester or solvate of any one of items 1 to 11, or the extract of any one of items 17-22, or the fraction of item 23, or the composition of item 27 or 28 for use in the treatment of a bacterial infection (e.g., a *Staphylococcus* such as *Staphylococcus aureus* (e.g., wild type or MRSA) or *Staphylococcus epidermidis*).

30. A method of treating a bacterial infection (e.g., a *Staphylococcus* such as *Staphylococcus aureus* (e.g., wild type or MRSA) or *Staphylococcus epidermidis*), the method comprising the step of administering an effective amount of (i) the compound of any one of items 1 to 11, or (ii) a pharmaceutically acceptable salt, ester or solvate of (i), or (iii) the extract of any one of items 17-22; or (iv) the fraction of item 23, or (v) the composition of item 27 or 28 to a subject in need thereof.

31. The method of item 30, wherein the subject is a human.

32. The method of item 30, wherein the subject is a non-human animal.

DETAILED DESCRIPTION OF THE INVENTION

Figure 1:
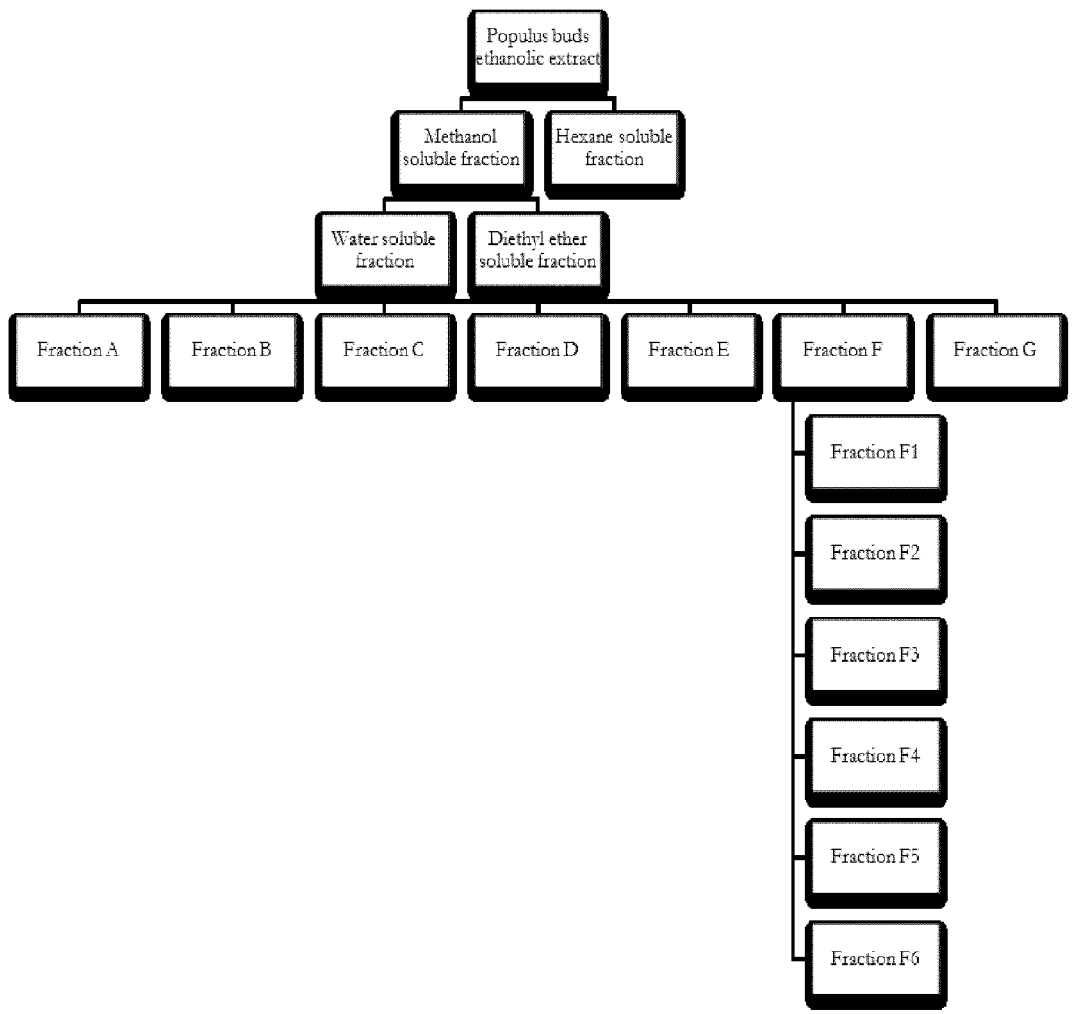
FIG. 1 shows the fractionation scheme of *Populus balsamifera* bud extract according to an embodiment of the invention.
Figure 2:
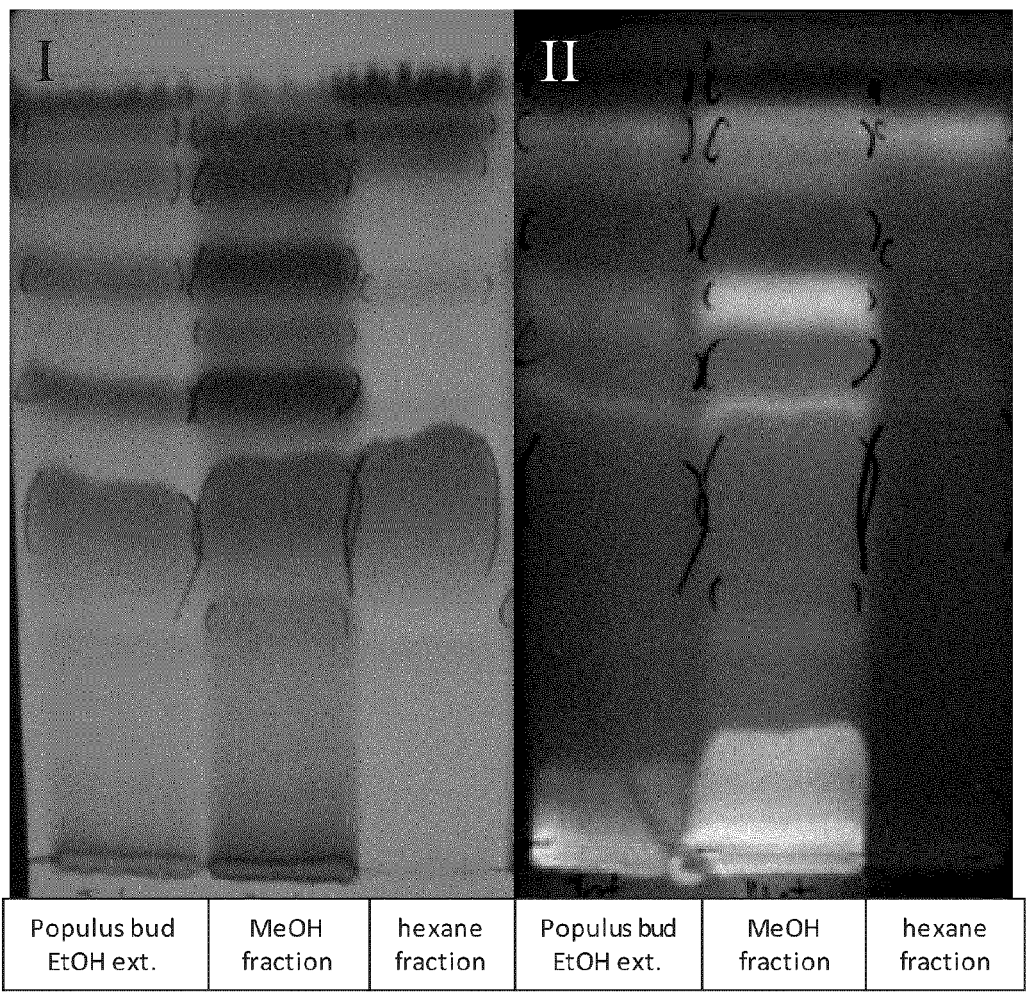
FIG. 2 shows the thin layer chromatograms obtained from the *Populus Balsamifera* buds ethanolic extract and the methanol soluble and hexane soluble fractions. Elution was conducted in 15:1 CHCl$_3$-MeOH mixture and visualized under UV 254 nm (I) and under UV 365 nm after treatment with 1% methanolic diphenylboryloxyethylamine (NP) followed by 5% polyethylene glycol-4000 (PEG) (II)
Figure 3:
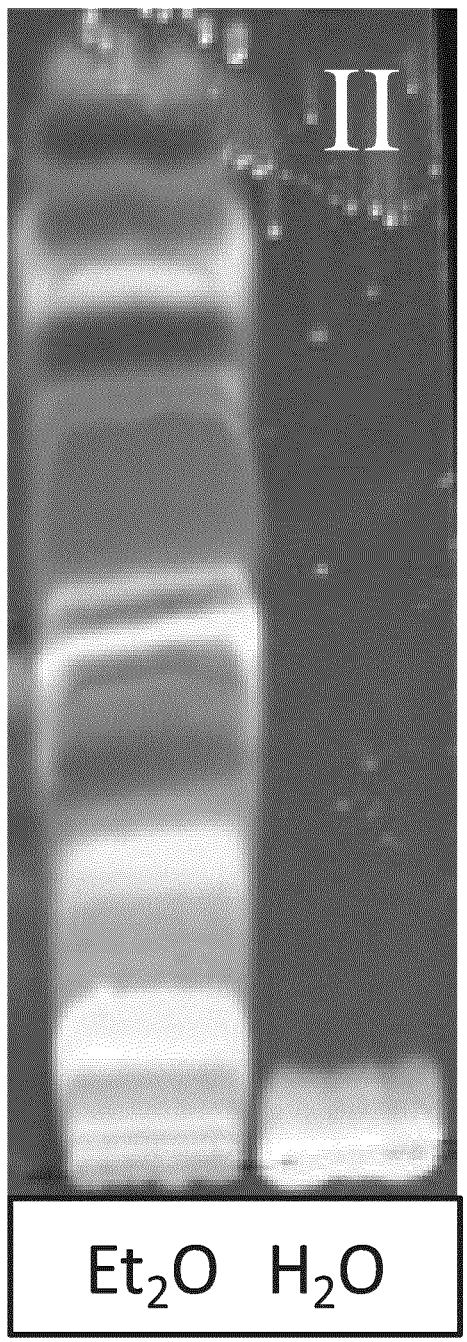
FIG. 3 shows the thin layer chromatograms obtained from the diethyl ether soluble and water soluble fractions visualized under UV 365 nm after treatment with 1% methanolic diphenylboryloxyethylamine (NP) followed by 5% polyethylene glycol-4000 (PEG)
Figure 4:
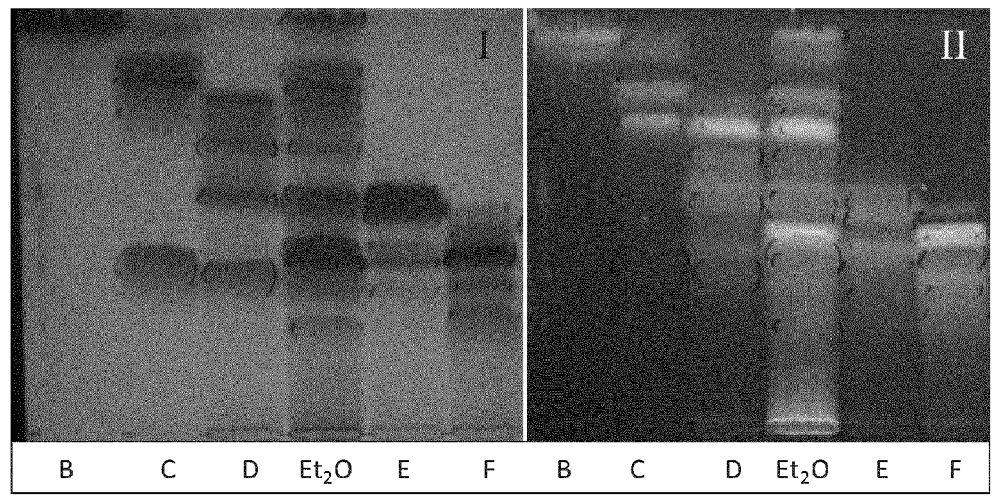
FIG. 4 shows the thin layer chromatograms obtained from fractions B, C, D, E and F. Elution was conducted in 15:1 CHCl$_3$-MeOH mixture and visualized under UV 254 nm (I) and under UV 365 nm after treatment with 1% methanolic diphenylboryloxyethylamine (NP) followed by 5% polyethylene glycol-4000 (PEG) (II)

Turning now to the invention in more details, there is provided compounds of FORMULA (I) and salts, esters and solvates thereof, in particular, pharmaceutically acceptable salts, esters and solvates thereof. Compounds of formula (I) have the following general structure:

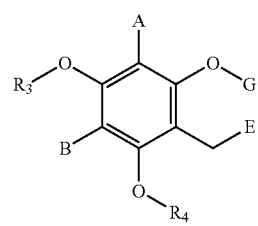

wherein:
one of A and B is H and the other is

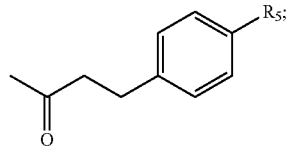

and
G is $R_2$ and E is

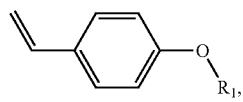

or
G and E are both carbon atoms, said carbon atoms being linked together by a single bond, G being substituted by

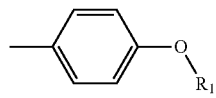

and E being substituted by $R_6$.

For clarity, in the above chemical formula FORMULA (I) when G and E are both carbon atoms, said carbon atoms being linked together by a single bond, G being substituted by

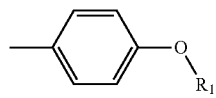

and E being substituted by $R_6$, they form formula (II):

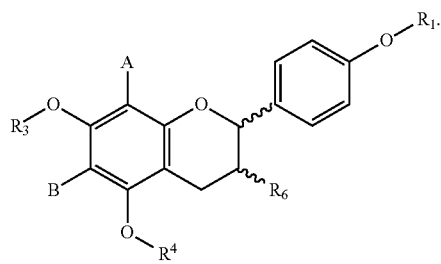

In embodiments of the compounds of FORMULA (II), A, B, $R_1$, $R_3$, $R_4$ and $R_6$ are as defined in FORMULA I.

Compounds of formula (I) include compounds of FORMULAS 1, 2 and 3 as shown below. The salts, esters and solvates of these compounds, in particular, pharmaceutically acceptable salts, esters and solvates are also covered by the invention.

Compounds of FORMULA 1 have the following general structure:

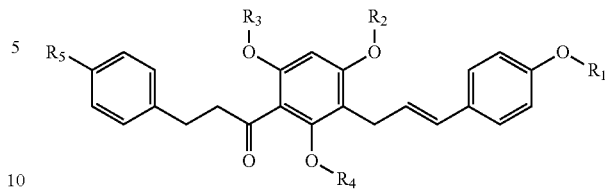

Compounds of FORMULA 2 have the following general structure:

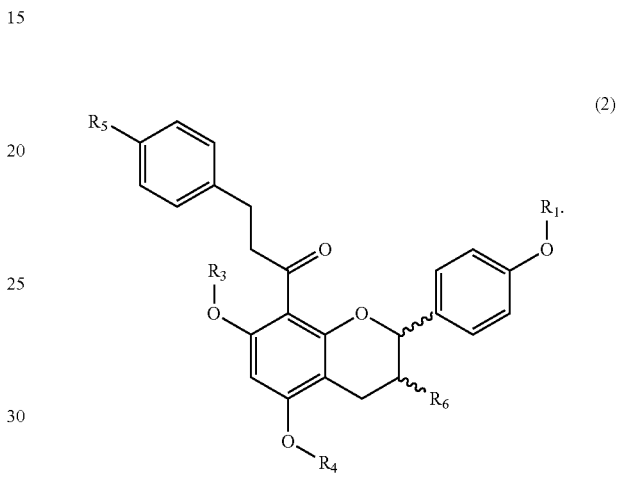

Compounds of FORMULA 3 have the following general structure:

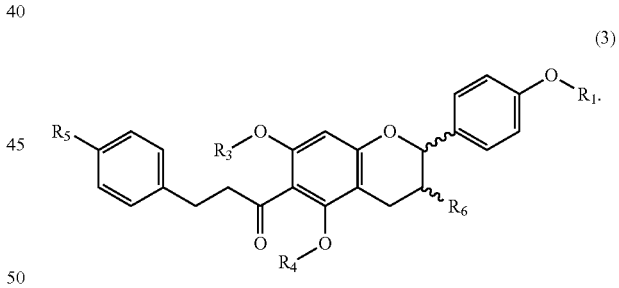

In the above formulas (I), (II), (1), (2) and (3), each of $R_1$, $R_2$, $R_3$, and $R_4$ can independently be H or alkyl; and each of $R_5$ and $R_6$, can independently be H, OH, alkyl, or alkoxy, Herein, the term "alkyl" refers to saturated hydrocarbons of formula —$C_nH_{2n-1}$. In embodiments, the alkyl is branched or linear has a number of carbon atoms between 1 and 12, and more specifically between 1 and 6. In embodiments, the alkyl is methyl or ethyl.

Herein, the term "alkoxy" refers to —O-alkyl groups. In embodiments, alkoxy is methoxy.

In specific embodiments of the above, $R_1$ is H; if present, $R_2$ is H or —$CH_3$; $R_3$ is H; $R_4$ is H or $CH_3$; $R_5$ is H, —OH or —O—$CH_3$; if present $R_6$ is H or —OH.

In embodiments, the compounds of FORMULA 1 are:

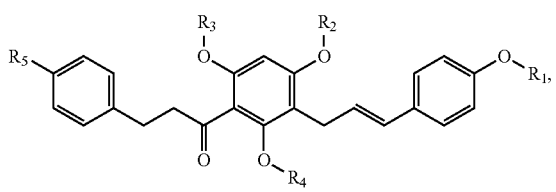

wherein:

| $R_1$ | $R_2$ | $R_3$ | $R_4$ | $R_5$ |
|---|---|---|---|---|
| H | $CH_3$ | H | H | OH; |
| H | H | H | H | —$OCH_3$; or |
| H | H | H | H | H. |

In embodiments, the compounds of FORMULA 2 are:

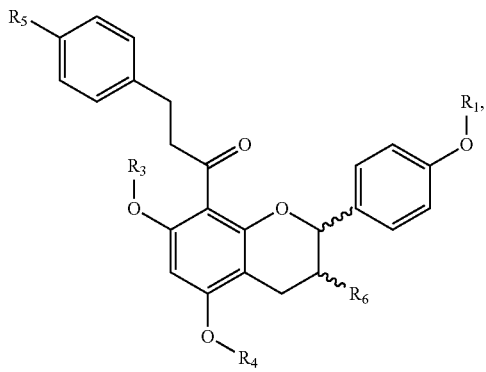

wherein:

| $R_1$ | $R_4$ | $R_3$ | $R_5$ | $R_6$ | Stereochemistry |
|---|---|---|---|---|---|
| H | H | H | H | H | Racemic; |
| H | H | H | H | H | 2S; |
| H | H | H | H | H | 2R; |
| H | H | H | —O—$CH_3$ | H | Racemic; |
| H | H | H | —O—$CH_3$ | H | 2S; |
| H | H | H | —O—$CH_3$ | H | 2R; |
| H | $CH_3$ | H | OH | H | Racemic; |
| H | $CH_3$ | H | OH | H | 2S; |
| H | $CH_3$ | H | OH | H | 2R; |
| H | H | H | H | OH | Racemic; |
| H | H | H | H | OH | 2S, 3S; |
| H | H | H | H | OH | 2S, 3R; |
| H | H | H | —O—$CH_3$ | OH | Racemic; |
| H | H | H | —O—$CH_3$ | OH | 2R, 3S; or |
| H | H | H | —O—$CH_3$ | OH | 2S, 3R. |

In embodiments, the compounds of FORMULA 3 are:

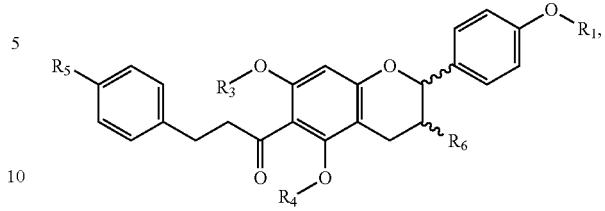

wherein:

| $R_1$ | $R_3$ | $R_4$ | $R_5$ | $R_6$ | Stereochemistry |
|---|---|---|---|---|---|
| H | H | H | H | OH | Racemic; |
| H | H | H | H | OH | 2R, 3S; or |
| H | H | H | H | OH | 2S, 3R. |

Isomers, Tautomers and Polymorphs:

As used herein, the term "isomers" refers to optical isomers (enantiomers), diastereoisomers as well as the other known types of isomers.

Some of the compounds of the invention have at least one asymmetric carbon atoms and can therefore exist in the form of optically pure enantiomers (optical isomers), as racemates and as mixtures thereof. Some of the compounds have at least two asymmetric carbon atoms and can therefore exist in the form of pure diastereoisomers and as mixtures thereof. It is to be understood, that, unless otherwise specified, the present invention embraces the racemates, the enantiomers and/or the diastereoisomers of the compounds of the invention as well as mixtures thereof.

In addition, the present invention embraces all geometric and positional isomers. For example, when a compound of the invention incorporates a double bond or a fused ring, both the cis- and trans-forms, as well as mixtures, are embraced within the scope of the invention.

Within the present invention, it is to be understood that a compound of the invention may exhibit the phenomenon of tautomerism and that the formula drawings within this specification can represent only one of the possible tautomeric forms. It is to be understood that the invention encompasses any tautomeric form and is not to be limited merely to any one tautomeric form utilized within the formula drawings.

It is also to be understood that certain compounds of the invention may exhibit polymorphism, and that the present invention encompasses all such forms.

Salts

The present invention relates to the compounds of the invention as hereinbefore defined as well as to salts thereof. The term "salt(s)", as employed herein, denotes basic salts formed with inorganic and/or organic bases. Salts for use in pharmaceutical compositions will be pharmaceutically acceptable salts, but other salts may be useful in the production of the compounds of the invention. The term "pharmaceutically acceptable salts" refers to salts of compounds of the present invention that are pharmacologically acceptable and substantially non-toxic to the subject to which they are administered. More specifically, these salts retain the biological effectiveness and properties of the antibiotic compounds of the invention and are formed from suitable non-toxic organic or inorganic acids or bases.

For example, where the compounds of the invention are sufficiently acidic, the salts of the invention include base salts formed with an inorganic or organic base. Such salts include alkali metal salts such as sodium, lithium, and potassium salts; alkaline earth metal salts such as calcium and magnesium salts; metal salts such as aluminium salts, iron salts, zinc salts, copper salts, nickel salts and a cobalt salts; inorganic amine salts such as ammonium or substituted ammonium salts, such as e.g., trimethylammonium salts; and salts with organic bases (for example, organic amines) such as chloroprocaine salts, dibenzylamine salts, dicyclohexylamine salts, dicyclohexylamines, diethanolamine salts, ethylamine salts (including diethylamine salts and triethylamine salts), ethylenediamine salts, glucosamine salts, guanidine salts, methylamine salts (including dimethylamine salts and trimethylamine salts), morpholine salts, morpholine salts, N,N'-dibenzylethylenediamine salts, N-benzyl-phenethylamine salts, N-methylglucamine salts, phenylglycine alkyl ester salts, piperazine salts, piperidine salts, procaine salts, t-butyl amines salts, tetramethylammonium salts, t-octylamine salts, tris-(2-hydroxyethyl) amine salts, and tris(hydroxymethyl)aminomethane salts. Preferred salts include those formed with sodium, lithium, potassium, calcium and magnesium.

Such salts can be formed routinely by those skilled in the art using standard techniques. Indeed, the chemical modification of a pharmaceutical compound (i.e. drug) into a salt is a technique well known to pharmaceutical chemists, (See, e.g., H. Ansel et. al., Pharmaceutical Dosage Forms and Drug Delivery Systems (6th Ed. 1995) at pp. 196 and 1456-1457, incorporated herein by reference). Salts of the compounds of the invention may be formed, for example, by reacting a compound of the invention with an amount of acid or base, such as an equivalent amount, in a medium such as one in which the salt precipitates or in an aqueous medium followed by lyophilization.

Esters

The present invention relates to the compounds of the invention as hereinbefore defined as well as to the esters thereof. The term "ester(s)", as employed herein, refers to compounds of the invention or salts thereof in which hydroxy groups have been converted to the corresponding esters using, for example, inorganic or organic anhydrides, acids, or acid chlorides. Esters for use in pharmaceutical compositions will be pharmaceutically acceptable esters, but other esters may be useful in the production of the compounds of the invention.

The term "pharmaceutically acceptable esters" refers to esters of the compounds of the present invention that are pharmacologically acceptable and substantially non-toxic to the subject to which they are administered. More specifically, these esters retain the biological effectiveness and properties of the antibiotic compounds of the invention and act as prodrugs which, when absorbed into the bloodstream of a warm-blooded animal, cleave in such a manner as to produce the parent alcohol compound.

Esters of the present compounds include among others the following groups (1) carboxylic acid esters obtained by esterification of the hydroxy groups, in which the non-carbonyl moiety of the carboxylic acid portion of the ester grouping is selected from straight or branched chain alkyl (for example, ethyl, n-propyl, t-butyl, n-butyl, methyl, propyl, isopropyl, butyl, isobutyl or pentyl), alkoxyalkyl (for example, methoxymethyl, acetoxymethyl and 2,2-dimethylpropionyloxymethyl), aralkyl (for example, benzyl), aryloxyalkyl (for example, phenoxymethyl), aryl (for example, phenyl optionally substituted with, for example, halogen, $C_{1-4}$ alkyl, or $C_{1-4}$ alkoxy or amino); (2) sulfonate esters, such as alkyl- or aralkylsulfonyl (for example, methanesulfonyl); (3) amino acid esters (for example, L-valyl or L-isoleucyl); (4) phosphonate esters; (5) mono-, di- or triphosphate esters (including phosphoramidic cyclic esters). The phosphate esters may be further esterified by, for example, a $C_{1-20}$ alcohol or reactive derivative thereof, or by a 2,3-di($C_{6-24}$)acyl glycerol. (6) Carbamic acid ester (for example N-methylcarbamic ester); and (7) Carbonic acid ester (for example methylcabonate)

Further information concerning examples of and the use of esters for the delivery of pharmaceutical compounds is available in Design of Prodrugs. Bundgaard H ed. (Elsevier, 1985), incorporated herein by reference. See also, H. Ansel et. al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp. 152-191; Jarkko Rautio et al., Nat. Rev. Drug Discov., 7, pp. 255-270 (2008); and Pen-Wei Hsieh et al., Curr. Pharm. Des., 15 (19), pp. 2236-2250 (2009), all incorporated herein by reference.

The compounds of this invention may be esterified by a variety of conventional procedures including reacting the appropriate anhydride, carboxylic acid or acid chloride with the alcohol group of a compound of this invention. For example, an appropriate anhydride may be reacted with an alcohol in the presence of a base, such as 1,8-bis[dimethylamino]naphthalene or N,N-dimethylaminopyridine, to facilitate acylation. Also, an appropriate carboxylic acid can be reacted with the alcohol in the presence of a dehydrating agent such as dicyclohexylcarbodiimide, 1-[3-dimethylaminopropyl]-3-ethylcarbodiimide or other water soluble dehydrating agents which are used to drive the reaction by the removal of water, and, optionally, an acylation catalyst. Esterification can also be effected using the appropriate carboxylic acid. Reaction of an acid chloride with the alcohol can also be carried out. When a compound of the invention contains a number of free hydroxy group, those groups not being converted into a prodrug functionality may be protected (for example, using a t-butyl-dimethylsilyl group), and later deprotected. Also, enzymatic methods may be used to selectively phosphorylate or dephosphorylate alcohol functionalities. One skilled in the art would readily know how to successfully carry out these as well as other known methods of esterification of alcohols.

Esters of the compounds of the invention may form salts. Where this is the case, this is achieved by conventional techniques as described above.

Solvates

The compounds of the invention may exist in unsolvated as well as solvated forms with solvents such as water, ethanol, and the like, and it is intended that the invention embrace both solvated and unsolvated forms.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Solvates for use in pharmaceutical compositions will be pharmaceutically acceptable solvates, but other solvates may be useful in the production of the compounds of the invention.

As used herein, the term "pharmaceutically acceptable solvates" means solvates of antibiotic compounds of the present invention that are pharmacologically acceptable and substantially non-toxic to the subject to which they are administered. More specifically, these solvates retain the biological effectiveness and properties of the antibiotic compounds of the invention and are formed from suitable non-toxic solvents.

Non-limiting examples of suitable solvates include ethanolates, methanolates, and the like, as well as hydrates, which are solvates wherein the solvent molecules are $H_2O$.

Preparation of solvates is generally known. Thus, for example, M. Caira et al, J. Pharmaceutical Sci., 93(3), 601-611 (2004), incorporated herein by reference, describe the preparation of the solvates of the antifungal fluconazole in ethyl acetate as well as from water. Similar preparations of solvates, hemisolvate, hydrates and the like are described by E. C. van Tonder et al, AAPS Pharm Sci Tech., 5(1), article 12 (2004); and A. L. Bingham et al, Chem. Commun., 603-604 (2001), both incorporated herein by reference.

A typical, non-limiting, process for preparing a solvate involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, can be used to show the presence of the solvent (or water) in the crystals as a solvate (or hydrate).

Extracts

In an embodiment, there is also provided an extract or a fraction thereof from buds of *Populus balsamifera* (commonly called balsam poplar) or of another *Populus* species. *Populus* is a genus of 25-35 species of deciduous flowering plants in the family Salicaceae, native to most of the Northern Hemisphere. English names variously applied to these species include poplar, aspen, and cottonwood. Examples of other *Populus* species include those in the *Tacamahaca* section of this genus, such as *Populus Trichocarpa* (also known as black cottonwood, western balsam poplar or California poplar).

The above extract comprises at least one (one or more: at least two, at least three, etc.) of the compounds of the invention as described herein.

Preparation

Grinding: In embodiment, the *Populus* (e.g., *Populus balsamifera*) buds may first be coarsely grinded using an electrical blender or mortar and pestle. It may optionally be first soaked in liquid nitrogen to freeze resin. Other methods known in the art for grinding may be used.

The grinded buds are then first extracted using a first solvent.

In an embodiment, the extract or fraction thereof is an aqueous extract or fraction thereof. In another embodiment, it is an hydroalcoholic extract or fraction thereof. In a more specific embodiment, it is an ethanolic or methanolic extract or fraction thereof or an extract obtained from a $C_{1-10}$ aliphatic alcohol or a fraction thereof. In another embodiment, the extract is an extract obtained using an organic solvent, examples of which include ketones (such as $C_{1-10}$ ketones), hydrocarbons (such as hexane), organic acids, esters (such as ethyl acetate), ethers (such as ethyl ether), alkyl chlorides (such as methylene chloride), etc. A mixture of any two or more of the foregoing solvents may be used. The first solvent is evaporated to generate a first extract/residue.

Non polar components/impurities. Additional extractions/suspensions may then be carried out to remove non-polar components/impurities of the first extract/residue. This additional extraction is performed with a second solvent (or mixture of solvents) on the first extract/residue obtained with the first solvent (or mixture of solvents). In an embodiment, the first extract/residue obtained with the first solvent (or mixture of solvents) is suspended in methanol and extracted with an alkane that is non-soluble in methanol (e.g., hexane, pentane, or petroleum ether). The non-polar components/impurities are thus solubilized with the alkane (e.g., hexane) phase which is then discarded. The methanol phase is then evaporated to generate a second extract/residue.

Polar components/impurities. In an embodiment, the second residue/extract obtained with the second solvent (or mixture of solvents) is subjected to a third suspension/extraction to remove polar components/impurities of the second extract/residue. For instance, the second extract/residue can be suspended in diethyl ether, butanol or chlorinated solvents such as chloroform or chloromethane and extracted with water. In an embodiment, the residue is suspended in $Et_2O$ and extracted with water. The polar components/impurities are thus solubilized with the water phase which is then discarded. The e.g., diethyl ether phase is then evaporated to generate a third extract/residue.

The extract can be in a liquid or dried form.

In more specific embodiments, the extract is an ethanolic extract of *Populus balsamifera* buds (or a combination of several such extracts) in liquid form or dried form. In more specific embodiments, there is provided a methanolic extract of the above-cited dried ethanolic extract, said methanolic extract having optionally being extracted with hexane one or more times. This methanolic extract can be in liquid or dry form. In even more specific embodiments, there is provided a diethyl ether extract of the above dried methanolic extract, said diethyl ether extract having optionally been extracted with water one or more times. This diethyl ether extract can be in liquid or dry form. In embodiments, there is provided one or more fractions obtained by chromatographic separation of this dried diethyl ethyl extract.

In embodiments, a preliminary extraction (i.e. prior to the first extraction (e.g., ethanol extraction)) can be performed on the matrix to remove undesirable compounds. For example, hexane or another solvent (e.g., hexane, ether, pentane or petroleum ether) could be used to remove non-polar compounds, such as waxy compounds. The first extraction can then be performed on the cleaned matrix.

Specific illustrations of extracts and fractions of the present invention are described in Examples presented herein. Extracts and fractions are described herein may be used in the treatment of bacterial infections as described herein.

Medicaments and Pharmaceutical Compositions

The present invention also relates to the use of the above-mentioned compounds of the invention and their pharmaceutically acceptable salts, esters and solvates thereof as well as the use of the above extracts of the invention in the preparation of a medicament.

The present invention also relates to pharmaceutical compositions comprising the above-mentioned compounds of the invention and their pharmaceutically acceptable salts, esters and solvates thereof and/or the above extracts of the invention.

Without being so limited, the medicaments/pharmaceutical compositions of the invention may be administered orally, for example in the form of tablets, coated tablets, dragees, hard or soft gelatin capsules, solutions, emulsions or suspensions. Administration can also be carried out rectally, for example using suppositories; locally, topically, or percutaneously, for example using ointments, creams, gels or solutions; or parenterally, e.g., intravenously, intramuscularly, subcutaneously, intrathecally or transdermally, using for example injectable solutions. Furthermore, administration can be carried out sublingually, nasally, or as ophthalmological preparations or an aerosol, for example in the form of a spray, such as a nasal spray.

For the preparation of tablets, coated tablets, dragees or hard gelatin capsules, the compounds of the present invention may be admixed with any known pharmaceutically inert, inorganic or organic excipient and/or carrier. Examples of suitable excipients/carriers include lactose, maize starch or derivatives thereof, talc or stearic acid or salts thereof.

As used herein the terms "subject in need thereof" refer to a subject who would benefit from receiving an effective amount of the compound of the present invention. It refers to an animal and to a human in a specific embodiment. The compounds of the present invention may also be used for veterinary applications and be used in pets or other animals (e.g., pets such as cats, dogs, horses, etc.; and cattle, fishes, swine, poultry, etc.).

Suitable excipients for use with soft gelatin capsules include for example vegetable oils, waxes, fats, semi-solid or liquid polyols etc. According to the nature of the active ingredients it may however be the case that no excipient is needed at all for soft gelatin capsules.

For the preparation of solutions and syrups, excipients which may be used include for example water, polyols, saccharose, invert sugar and glucose.

For injectable solutions, excipients which may be used include for example water, saline, alcohols, polyols, glycerine, vegetable oils and other appropriate excipients.

For suppositories, and local or percutaneous application, excipients which may be used include for example natural or hardened oils, waxes, fats and semi-solid or liquid polyols.

The medicaments/pharmaceutical compositions may also contain preserving agents, solubilizing agents, stabilizing agents, wetting agents, emulsifiers, sweeteners, colorants, odorants, salts for the variation of osmotic pressure, buffers, coating agents or antioxidants. They may also contain other therapeutically active agents.

Intravenous, intramuscular or oral administrations are preferred forms of use. The dosages in which the compounds of the invention are administered in effective amounts depend on the nature of the specific active ingredient, the age and the requirements of the patient and the mode of application.

As mentioned above, the pharmaceutical compositions of the invention can contain a pharmaceutically acceptable carrier including, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. Pharmaceutically acceptable carriers also can include physiologically acceptable aqueous vehicles (e.g., physiological saline) or other known carriers appropriate to specific routes of administration.

The compounds of the invention may be incorporated into dosage forms in conjunction with any of the vehicles which are commonly employed in pharmaceutical preparations, e.g., talc, gum arabic, lactose, starch, magnesium searate, cocoa butter, aqueous or non-aqueous solvents, oils, paraffin derivatives or glycols. Emulsions such as those described in U.S. Pat. No. 5,434,183, incorporated herein by reference, may also be used in which vegetable oil (e.g., soybean oil or safflower oil), emulsifying agent (e.g., egg yolk phospholipid) and water are combined with glycerol. Methods for preparing appropriate formulations are well known in the art (see e.g., Remington's Pharmaceutical Sciences, 16th Ed., 1980, A. Oslo Ed., Easton, Pa. incorporated herein by reference).

In cases where parenteral administration is elected as the route of administration, preparations containing the compounds of the invention may be provided to patients in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles may include fluid and nutrient replenishers, electrolyte replenishers, such as those based upon Ringer's dextrose, and the like.

It is a prerequisite that all adjuvants used in the manufacture of the preparations, such as carriers, are non-toxic and more generally pharmaceutically acceptable.

As used herein, "pharmaceutically acceptable" such as pharmaceutically acceptable carrier, excipient, etc., means pharmacologically acceptable and substantially non-toxic to the subject to which the particular compound is administered.

Any amount of a pharmaceutical composition can be administered to a subject. The dosages will depend on many factors including the mode of administration. Typically, the amount of the compound of the invention contained within a single dose will be an amount that effectively prevent, delay or treat the disease or condition to be treated, delayed or prevented without inducing significant toxicity.

The effective amount of the compounds of the invention may also be measured directly. The effective amount may be given daily or weekly or fractions thereof. Typically, a pharmaceutical composition of the invention can be administered in an amount from about 0.001 mg up to about 500 mg per kg of body weight per day (e.g., 10 mg, 50 mg, 100 mg, or 250 mg). Dosages may be provided in either a single or multiple dosage regimen. For example, in some embodiments the effective amount may range from about 1 mg to about 25 grams of the composition per day, about 50 mg to about 10 grams of the composition per day, from about 100 mg to about 5 grams of the composition per day, about 1 gram of the composition per day, about 1 mg to about 25 grams of the composition per week, about 50 mg to about 10 grams of the composition per week, about 100 mg to about 5 grams of the composition every other day, and about 1 gram of the composition once a week.

These are simply guidelines since the actual dose must be carefully selected and titrated by the attending physician based upon clinical factors unique to each patient. The optimal daily dose will be determined by methods known in the art and will be influenced by factors such as the age of the patient and other clinically relevant factors. In addition, patients may be taking medications for other diseases or conditions. The other medications may be continued during the time that the pharmaceutical composition of the invention is given to the patient, but it is particularly advisable in such cases to begin with low doses to determine if adverse side effects are experienced.

The present invention also relates to the use of the above-mentioned medicament for treating bacterial infections in humans and animals (e.g., cats, dogs, horses, cattle, swine, etc.). More generally, the invention related to the use of the compounds of the invention and their pharmaceutically acceptable salts, esters and solvates for treating bacterial infections. Therefore, the present invention also relates to a method of treating a bacterial infection, the method comprising the step of administering an effective amount of the above compound or pharmaceutically acceptable salts, esters and solvates thereof to a subject in need thereof.

As used herein, "bacterial infection" means an infection caused by bacteria. Non limiting examples of common bacterial infections include sinusitis, strep throat, pneumonia, ear infections, sepsis, bladder infections, skin infections, nocosomial infections and chirurgical infections. In a specific embodiment it refers to infections by one or more *staphylococcus* species. Without being so limited, the *staphylococcus* usefully targeted by the compounds, compositions, extracts and fractions of the present invention includes S. aureus (wild type or MRSA), S. epidermidis, S. aureus, S. auricularis, S. capitis, S. caprae, S. felis, S. haemolyticus, S. hominis, S. hyicus, S. lugdunensis, S. pettenkoferi, S. saprophyticus, S. schleiferi, S. simulans, S. vitulus, S. warneri and S. xylosus.

As used herein, the terms "dihydrochalcone derivatives" designates compounds of the invention based on the skeleton of dihydrochalcones:

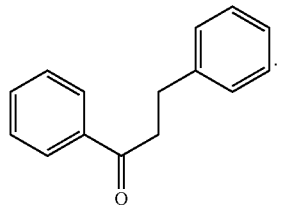 [SMILES: O=C(CCc1ccccc1)c1ccccc1]

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% of the numerical value qualified.

Unless otherwise defined, all technical and scientific terms used herein have the same meaning as commonly understood by one of ordinary skill in the art to which this invention belongs.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Example 1

Preparation of Compounds I, II, and III

Buds of *Populus balsamifera* (875 g) were crushed and then extracted under reflux with EtOH 95% (3×1.5 L), followed by EtOH 80% (3×1 L) and EtOH 70% (2×1 L). Ethanol was evaporated and the aqueous extract was treated with hexane to remove chlorophyll and other lipophilics compounds. After concentration of the aqueous phase, a dark brown syrup (284 g) was obtained.

The extract was subjected to column chromatography on Silica gel with a $CHCl_3$-MeOH gradient (40:1, 15:1, 5:1). Identical eluents were collected separately to obtain three rich fractions: 1F, 2F and 3F. Fraction 2F was chosen for further investigation.

The instrumentation used for HPLC analysis consisted of an Agilent™ 1100 series with a UV-MSD detector. Control of the equipment, data acquisition, processing and management of chromatographic information were performed with the Chemstation™ software (Agilent). The analytical HPLC separations were conducted on a Zorbax™ Eclipse ODS-C18 column (5 μm, 4.6×150 mm) and preparative HPLC separations on a Zorbax™ ODS-C18 column (7 μm, 21.2 mm×25 cm).

Analytical and preparative separation solvents were: water+0.1% HCOOH (solvent A) and acetonitrile+0.1% HCOOH (solvent B).

The gradient elution for analytical HPLC was carried out as follows: solvent B remained at 20% for 5 min, then solvent B was immediately increased to 35% and then gradually increased to 60% in 25 min. Finally, solvent B was gradually increased to 100% in 10 min. The injection volume was 20 μL (1 mg/ml). The flow rate was 1 ml/min and the UV absorbance was monitored at 300 nm.

The elution for preparative HPLC was carried out as follows: solvent B remained at 20% for 10 min, then solvent B was immediately increased to 35% and then gradually increased to 60% in 40 min. Finally, solvent B was gradually increased to 100% in 10 min. The flow rate was 16 ml/min and the injection volume was 300 μL (80 mg/ml).

Fraction 2F was subjected to HPLC separation, which led to the isolation of the following compounds:
Compound I (55 mg, TR=37.1 min),
Compound II (74 mg, TR=40.3 min), and
Compound III (39 mg, TR=41.4).

The isolated compounds were identified using their NMR spectra. These spectra were recorded on a Bruker Avance™ spectrometer ($^1H$ at 400.13 MHz; $^{13}C$ at 100.61 $MH_z$) equipped with a 5 mm QNP-probe. High resolution ESI-MS were carried out on an Applied Biosystems™/MDS Sciex QSTAR XL QqTOF MS system (serial #T0970304, Toronto, ON, Canada).

Compounds I, II and III were found to have the following general formula (1):

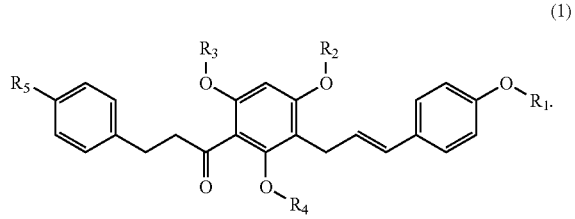

(1)

| Compound | $R_1$ | $R_2$ | $R_3$ | $R_4$ | $R_5$ |
|---|---|---|---|---|---|
| I | H | $CH_3$ | H | H | OH; |
| II | H | H | H | H | —$OCH_3$; or |
| III | H | H | H | H | H |

Materials and Methods

Bacteria Strain. Bacteria were provided by the Centre de sante et services sociaux de Chicoutimi, complexe hospitalier de la Sagamie. The *S. aureus* wild type strain was from ATCC (ATCC 25923). The MRSA were obtained as further described below.

Antibiotic agents. Cyprofloxacin and erythromycin were provided by Sigma-Aldrich. Gentamicin sulfate and vancomycin hydrochloride were provided by Calbiochem.

Antibiotic assay. The antibiotic assays were performed in 96-well plates (BD Falcon). The bacteria strains were inoculated in Nutrient Broth (BD) for the gram negative bacteria and Tryptic soy broth (BD) with 10% of defibrinated sheep blood (PML microbiological) for gram positive strain. All bacteria strains were dosed by spectrophotometry at 660 nm where 1 D.O=$2 \times 10^8$ bacteria/mL. All bacteria were plated in their respective broth at a concentration of 450 000 bacteria/mL.

Compounds I, II and III were diluted in methanol and the above-noted antibiotic agents were diluted in water. The solvent concentration was 0.25%, which was not toxic for the bacteria. Compounds I, II and III and the above-noted antibiotic agents were tested at 8 different concentrations.

Each well contained: 100 μL of bacteria, 50 μL of the compounds tested (compound I, II, III or the above-noted antibiotic agent) and 50 μL of a 4% resazurin (Sigma) solution. The plates were incubated at 37° C. for 5 h. The fluorescence was read using a Fluoroskan Ascent™ FL (thermo) using an excitation wavelength of 530 nm and an emission wavelength of 590 nm.

Cytotoxicity assay. The cytotoxicity assay was performed in 96-well plates (BD Falcon). The WS-1 cell lines were provided by ATCC. The WS-1 was cultured in DMEM+10% fetal calf serum. The cells were plated in a volume of 100 μL at a density of 5000 cells per well and incubated at 37° C.+5% $CO_2$ for 24 h to promote cell adhesion.

The compounds tested (compound I, II, III or the above-noted antibiotic agent) were then added at 8 different concentrations with a concentration of solvent of 0.25% to avoid solvent toxicity. The plates were incubated at 37° C.+5% $CO_2$ for 48 h. The cells were then washed with 100 μL of HBSS and 150 μL of a 2% resazurin were added to the wells.

The plates were again incubated at 37° C.+5% $CO_2$ for 1 h and their fluorescence was read using a Fluoroskan Ascent™ FL (thermo) using an excitation wavelength of 530 nm and an emission wavelength of 590 nm.

Antibiotic Activity and Cytotoxicity Against MRSA, Gram Negative and Gram Positive Strains Isolation and identification of methicillin-resistant *Staphylococcus aureus* (MRSA) strains. From March 2007 to March 2008, 35 screening swabs from nares (n=31), throat (n=3), Groin pus (n=1) were obtained from patients hospitalized at Chicoutimi hospital. Identification of *S. aureus* was performed using the Slidex Staph-Kit (bioMerieux Vitek, Inc., Hazelwood, Mo.) according to the manufacturer's instructions. Quality control was performed with MRSA strain ATCC 43300 and *S. aureus* strain ATCC 25923. In addition, *S. aureus* profile was determined with API Staph test strip with bacterial suspension of saline McFarland of 0.5 (bioMerieux, Durham, N.C.) according to the manufacturer's protocol. API Staph strips were held for 24 h before the results were read. A latex agglutination (SLIDEX) test detecting methicilin resistance in Staphylococci based on the production of low-affinity PBP2a, which is encoded by the mecA gene was performed on all strains. An antibiogram was also performed to confirm the identification of MRSA strains using disk diffusion test.

Antibiotic susceptibility testing using disk diffusion method. The antimicrobial activity of different classes of antibiotics of the potential MRSA was determined by diffusion method (Kirby-Bauer) as described by NCCLS. The antibiotics tested included: penicillin (10 units), amoxicillin/clavulanic acid (20/10 μg), ciprofloxacin (5 μg), moxifloxacin (5 μg), levofloxacin (5 μg), clindamycin (15 μg), erythromycin (15 μg), cefoxitin (30 μg), linezolid (30 μg), trimethoprim/sulfomethoxazole (1.25/23.75 μg), rifampicin (5 μg), gentamicin (10 μg) and vancomycin (30 μg). The agar medium had pH 7.2 to 7.4 before inoculing potentiel MRSA. The antibiotics were maintained at 8° C. or lower −14° C. according to manufacturer's recommendations. The pure culture was inoculated on a non-selective plate for 18-24 h. Each colony was collected with a wire loop and transfered the growth to a tube containing 4 to 5 mL of a tryptic-soy broth. The inoculum density was standarized with $BaSO_4$ using 0.5 McFarland standard. All strains were incubated at 37° C. until it achieves or exceeds the turbidity of 0.5 McFarland standard. Inoculation of the dried surface (Muller-Hinton agar plate) by streaking the swab over the entire sterile agar surface. This procedure was repeated two more times. After 15 min, the appropriate disk were applied on the surface with a sterile forceps. The inverted plates was placed in a incubator at 37° C./air/16 to 18 h or 24 h for vancomycin. The inhibition zones were measured with a millimetric ruler. Interpretation of zone sizes by references of the manufacturer. Quality control organisms used were ATCC strains number 25923.

MRSA. Ten (10) strains of MRSA obtained as described above were tested along with an *S. aureus* wild type (WT) strain (ATCC25923).

Table 2 shows that Compounds I, II and III had a similar $IC_{50}$ for MRSA and for *S. aureus* WT (ATCC25923). This indicates that the MRSA strains are not resistant to these compounds.

In contrast, all the $IC_{50}$ values for ciprofloxacin (control) against the MRSA strains were around 100-150 μM, while the $IC_{50}$ value against the wild type strain was 0.4±0.2 μM. This indicates that the MRSA strains used in the tests were resistant to ciprofloxacin.

With regard to the Minimum Inhibitory Concentration (MIC), compounds I, II and III had MIC values between 2.24 to 6.87 µM. The MIC of vancomycin (control) and that of compounds I, II and III against the wild type strain were similar.

Five additional strains were tested: *Streptococcus pneumoniae, Streptococcus agalactiae, Streptococcus pyogenes, Enterococcus faecalis* and *Corynebacterium jeikeium*. The results are shown in Table 4.

TABLE 2

Antibiotic activity of compounds I, II and III against 10 MRSA strains and against *S. aureus* wild type strain (ATCC 25923). $IC_{50}$ values are shown along their standard error. The Minimum Inhibitory Concentration (MIC) values are presented between parentheses. All values are in µM.[a]

| Strain | I | II | III | Ciprofloxacin | Vancomycin |
|---|---|---|---|---|---|
| MRSA1 | 2.2 ± 0.2 | 2.5 ± 0.2 | 2.4 ± 0.2 | 102 ± 6 | 0.08 ± 0.01 |
| | (5.11) | (5.34) | (5.5) | (>186) | (0.12) |
| MRSA2 | 2.2 ± 0.2 | 2.6 ± 0.2 | 2.3 ± 0.2 | 156 ± 11 | 0.08 ± 0.01 |
| | (5.22) | (5.57) | (4.89) | >186 | (0.13) |
| MRSA3 | 2.1 ± 0.2 | 2.6 ± 0.2 | 2.2 ± 0.2 | (>186) | 0.064 ± 0.007 |
| | (5.54) | (5.29) | (5.11) | >186 | (0.1) |
| MRSA4 | 2.1 ± 0.2 | 2.4 ± 0.1 | 2.2 ± 0.2 | 134 ± 7 | 0.069 ± 0.009 |
| | (4.82) | (4.61) | (4.53) | (>186) | (0.1) |
| MRSA5 | 1.7 ± 0.2 | 2.3 ± 0.4 | 2.3 ± 0.2 | 109 ± 4 | 0.062 ± 0.006 |
| | (5.07) | (4.86) | (4.27) | (>186) | (0.09) |
| MRSA6 | 2.0 ± 0.2 | 2.3 ± 0.2 | 2.2 ± 0.2 | 131 ± 9 | 0.08 ± 0.01 |
| | (5.01) | (5.22) | (5.03) | (>186) | (0.2) |
| MRSA7 | 2.1 ± 0.2 | 2.5 ± 0.2 | 2.4 ± 0.2 | 128 ± 9 | 0.08 ± 0.01 |
| | (4.39) | (4.34) | (4.93) | (>186) | (0.11) |
| MRSA8 | 2.1 ± 0.2 | 2.3 ± 0.2 | 2.2 ± 0.2 | 119 ± 9 | 0.08 ± 0.01 |
| | (4.64) | (4.84) | (4.98) | (>186) | (0.11) |
| MRSA9 | 2.3 ± 0.2 | 2.5 ± 0.2 | 2.3 ± 0.2 | 106 ± 11 | 0.08 ± 0.01 |
| | (5.00) | (5.26) | (5.77) | (>186) | (0.11) |
| MRSA10 | 2.6 ± 0.2 | 3.2 ± 0.2 | 2.8 ± 0.2 | 122 ± 16 | 0.059 ± 0.006 |
| | (5.15) | (5.07) | (5.31) | (>186) | (0.09) |
| *S. aureus* WT ATCC 25923 | 2.8 ± 0.9 | 2.7 ± 0.7 | 2.2 ± 0.6 | 0.4 ± 0.2 | 0.4 ± 0.2 |
| | (6.87) | (6.47) | (5.81) | (47.93) | (1.44) |

[a]Erythromycin and gentamicin were also tested as controls. The values obtained were greater than 200 µM for erythromycin and smaller than 1.56 µM for aentamicin and are not reported.

Two different strains of *Staphylococcus* were tested, namely the *S. epidermidis* and the *S. aureus* strains. The $IC_{50}$ and MIC values obtained are presented in Table 3.

Compounds I, II, and III had very similar $IC_{50}$ values. For these compounds, the $IC_{50}$ and the MIC values were somewhat smaller for the *S. aureus* strain than for the *S. epidermidis* strain. Compounds I, II, and III were more active than ciprofloxacin on *S. epidermidis*.

No activity against *Enterococcus faecalis* was detected for compounds I, II and III. The ciprofloxacin control was not active against the 14115 strain of this bacterium.

For *Streptococcus pneumoniae*, Compounds I, II and III were active against the 14070 strain. Compound I was active against strains 14112 and 14148. Only compound I and the vancomycin control had an activity against strain 14138. Compounds I, II and III and the ciprofloxacin control, were not active against strain 14144.

TABLE 3

Antibiotic activity of compounds I, II, and III on *staphylococcus* strains. $IC_{50}$ values are shown with their standard error. The Minimum Inhibitory Concentration (MIC) values are presented between parentheses. All values are in µM.

| Strain | I | II | III | Ciprofloxacin | Gentamicin | Vancomycin |
|---|---|---|---|---|---|---|
| *S. epidermidis* 14069 | 5.3 ± 0.2 (19.9) | 5.0 ± 0.3 (12.7) | 4.5 ± 0.3 (10.9) | 31 ± 2 (>200) | <0.006 (2.51) | 0.8 ± 0.1 (6.58) |
| *S. epidermidis* 14085 | 4.5 ± 0.3 (23.5) | 4.4 ± 0.3 (14.3) | 3.6 ± 0.4 (11.6) | 26.3 ± 0.8 (>200) | <0.006 (1.19) | 0.8 ± 0.1 (4) |
| *S. epidermidis* 14093 | 8.6 ± 0.6 (11.6) | 7.0 ± 0.3 (11.2) | 6.3 ± 0.6 (8.43) | <1.56 (77.1) | <0.006 (1.25) | 1.3 ± 0.2 (8.38) |
| *S. aureus* 14094 | 3.5 ± 0.3 (6.54) | 3.5 ± 0.3 (6.2) | 2.4 ± 0.2 (5.5) | <1.56 (87.6) | <0.006 (0.04) | 0.28 ± 0.04 (0.41) |
| *S. aureus* 14108 | 2.7 ± 0.3 (8.73) | 3.3 ± 0.2 (6.81) | 2.7 ± 0.2 (5.25) | <1.56 (66.8) | 0.016 ± 0.003 (0.05) | 0.27 ± 0.04 (0.44) |
| *S. aureus* 14118 | 3.5 ± 0.1 (5.27) | 5 ± 133 (5.05) | 2.3 ± 0.1 (3.46) | <1.56 (65.1) | 0.008 ± 0.001 (0.02) | 0.24 ± 0.03 (0.38) |
| *S. epidermidis* 14134 | 3.7 ± 0.4 (19) | 3.8 ± 0.6 (13.5) | 3.0 ± 0.6 (14.7) | 44 ± 1 (>200) | 0.13 ± 0.01 (0.8) | 1.7 ± 0.2 (11.4) |
| *S. epidermidis* 14143 | 6.7 ± 0.3 (15.2) | 5.8 ± 0.2 (10.9) | 4.41 ± 0.04 (9) | 80 ± 7 (>200) | 0.20 ± 0.03 (>2) | 2.7 ± 0.1 (>12.5) |
| *S. aureus* 14154 | 2.3 ± 0.1 (4.37) | 2.0 ± 0.1 (4.88) | 1.5 ± 0.1 (4.95) | <1.56 µM (25.1) | <0.016 (0.04) | 0.28 ± 0.05 (0.45) |

For *Streptococcus pyogenes* strain 14149, only compound I was active with an $IC_{50}$ of 118 µM. For strain 14152, compounds I, II and III were all active.

For *Streptococcus agalactiae*, compounds I, II and III were active against strain 14150. For strain 14151, only compound I was found active with an $IC_{50}$ value of 198±3 µM.

The last strain tested was *Corynebacterium jeikeium*. Compounds I, II and III were active with $IC_{50}$ values between 9 to 33 µM.

TABLE 4

Antibiotic activity of compounds I, II, and III on *Streptococcus*, *enterococcus* and *corynebacterium* strains. The IC50 values are shown with their standard error. The Minimum Inhibitory Concentration (MIC) values are presented between parentheses. All values are in µM.

| Strain | I | II | III | Ciprofloxacin | Gentamicin | Vancomycin |
|---|---|---|---|---|---|---|
| Strep. pneumoniae 14070 | 29 ± 5 (74.1) | 54 ± 4 (122) | 124 ± 5 (>200) | >200 (>200) | 4 ± 2 (>20) | 0.09 ± 0.04 (8.37) |
| Ent. Faecalis 14078 | >200 (>200) | >200 (>200) | >200 (>200) | 15 ± 2 (>200) | 11 ± 1 (>20) | 0.7 ± 0.1 (5.59) |
| Strep. pneumoniae 14112 | 29 ± 3 (66.2) | 74 ± 6 (169) | 89 ± 5 (190) | 63 ± 6 (200) | >20 (>20) | 0.094 ± 0.008 (0.16) |
| Ent. Faecalis 14115 | >200 (>200) | >200 (>200) | >200 (>200) | >200 (>200) | >20 (>20) | >10 (>10) |
| Strep. pneumoniae 14138 | 142 ± 12 (>200) | >200 (>200) | >200 (>200) | >200 (>200) | >20 (>20) | 0.13 ± 0.08 (>10) |
| Coryne. jeikeium 14139 | 14 ± 3 (67.5) | 33 ± 3 (112) | 9 ± 2 (200) | 1.42 ± 0.07 (16.4) | 0.92 ± 0.07 (9.1) | 0.22 ± 0.03 (0.35) |
| Strep. pneumoniae 14144 | >200 (>200) | >200 (>200) | >200 (>200) | >200 (>200) | >20 (>20) | >10 (>10) |
| Strep. pneumoniae 14148 | 40 ± 4 (81.2) | 83 ± 7 (200) | 93 ± 7 (200) | 56 ± 6 (200) | >20 (>20) | 0.084 ± 0.006 (0.2) |
| Strep. pyogenes 14149 | 118 ± 50 (200) | >200 (>200) | >200 (>200) | 43 ± 2 (169) | >20 (>20) | 0.117 ± 0.009 (0.17) |
| Strep. agalactiae 14150 | 144 ± 2 (200) | 169 ± 3 (>200) | 154 ± 2 (>200) | 138 ± 10 (>200) | >20 (>20) | 0.25 ± 0.06 (0.35) |
| Strep. agalactiae 14151 | 198 ± 3 (>200) | >200 (>200) | >200 (>200) | >200 (>200) | >20 (>20) | 0.33 ± 0.06 (4.03) |
| Strep. pyogenes 14152 | 44 ± 10 (>200) | 90 ± 7 (>200) | 174 ± 10 (>200) | 0.6 ± 1.0 (37.4) | >20 (>20) | 0.08 ± 0.02 (3.25) |
| Strep. agalactiae 14153 | 174 ± 3 (>200) | >200 (>200) | >200 (>200) | 190 ± 10 (>200) | >20 (>20) | 0.24 ± 0.04 (0.36) |

Therapeutic Index

The therapeutic index is the ratio between the toxicity on normal cells, in this case fibroblast, and the toxicity on bacteria. In Table 5, the therapeutic indexes of compounds I, II and III are presented.

TABLE 5

Therapeutic indexes of compounds I, II and III

| Compound | WS-1 | S. aureus WT ATCC 25923 | Therapeutic index |
|---|---|---|---|
| I | 49 ± 9 | 2.8 ± 0.9 | 18 |
| II | 27 ± 4 | 2.7 ± 0.7 | 10 |
| III | 20 ± 3 | 2.2 ± 0.6 | 9 |

Example 2

Preparation of Compounds IV to XXI

Buds previously immersed in liquid nitrogen were coarsely ground using an electrical blender. The resulting crude powder (1036 g) was extracted 5 times (5 h each time) with 2.5 L of 95% EtOH under reflux and extracts were combined. After evaporation of the solvent using a rotary evaporator, the residue was suspended in MeOH and extracted with hexanes. The dried MeOH residue (380.4 g) was suspended in $Et_2O$ and extracted with water.

The dried $Et_2O$ phase (355.1 g) was submitted to three successive fractionation steps: (1) silica gel column chromatography ($CHCl_3$-MeOH, 40:1-20:1-10:1-0:1, v:v); (2) silica gel column chromatography ($CHCl_3$-MeOH, 40:1-30:1-20:1-10:1-0:1, v:v); (3) C18 flash chromatography (MeOH—$H_2O$, 65:35-70:30-72:28-0:100, v:v). Third fractionation step afforded 5 fractions (A-E).

The instrumentation used for HPLC analysis consisted of an Agilent™ 1100 series with a UV-MSD detector. Control of the equipment, data acquisition, processing and management of chromatographic information were performed with the Chemstation™ software (Agilent). The analytical HPLC separations were conducted on a Inerstil™ Prep ODS column (6 mm×250 mm, 10μ) and preparative HPLC separations on a Inerstil™ Prep ODS column (20 mm×250 mm, 10μ). Chiral semi-preparative HPLC separation were conducted with a RegisPack™ chiral column (10.0 mm×250.0 mm, 5μ).

Fraction A (19.3 g) was suspended in a CHCl$_3$-EtOAc mixture (10:1, v:v, 100 ml) and filtrated. The filtrate was recovered, dried, and the residue (5.7 g) was submitted to silica gel cc (CHCl$_3$-EtOAC, 5:1-4:1-3:1-2:1-1:1, v:v, followed by MeOH) to afford 9 subfractions (A1 to A9). A1 (261.2 mg) was purified by semi-preparative HPLC (CH$_3$CN—H$_2$O, 50:50) to yield a racemic mixture IV (58.3 mg) which was purified by chiral semi-preparative HPLC (Hexane-IPA, 92:8) to afford V (15.9 mg) and VI (18.5 mg). A2 (152.5 mg) was submitted to semi-preparative HPLC (CH$_3$CN—H$_2$O, 50:50) to obtain a racemic mixture VII (18.3 mg) which was purified by chiral semi-preparative HPLC (hexane-IPA, 92:8) to afford VIII (8.6 mg) and IX (6.1 mg). A3 (119.7 mg) was applied to a preparative HPLC (MeOH—H$_2$O, 80:20→100:0, 30.00 min.) to yield racemic mixture X (30.0 mg) which was purified by chiral preparative HPLC (hexane-IPA, 90:10) to obtain XI (6.5 mg) and XII (6.1 mg). A4 (545.0 mg) was subjected to two semi-preparative HPLC purification steps [(1) MeOH—H$_2$O, 75:25, v:v; (2) CH$_3$CN—H$_2$O, 50:50, v:v] to obtain racemic mixture XIII (15.2 mg) which was submitted to chiral semi-preparative HPLC (hexane-IPA, 85:15) to yield XIV (3.4 mg) and XV (2.5 mg). A7 (244.9 mg) was subjected to semi-preparative HPLC (MeOH—H$_2$O, 60:40, v:v) to obtain racemic mixture XVI (32.0 mg) which was purified by chiral semi-preparative HPLC (hexane-IPA, 90:10) to afford XVII (12.2 mg) and XVIII (12.6 mg). A8 (90.1 mg) and A9 (118.9 mg) were subjected to semi-preparative HPLC (CH$_3$CN—H$_2$O, 40:60) and further purified by another semi-preparative HPLC (MeOH—H$_2$O, 65:35, v:v) to obtain racemic mixture XIX (11.4 mg) which was separated by chiral semi-preparative HPLC (hexane-IPA, 85:15) to yield XX (1.5 mg) and XXI (1.2 mg).

The isolated compounds were identified using their NMR spectra. These spectra were recorded on a Bruker Avance™ spectrometer ($^1$H at 400.13 MHz; $^{13}$C at 100.61 MHz) equipped with a 5 mm QNP-probe. High resolution ESI-MS were carried out on an Agilent Technologie™ 6210 TOF MS system. Absolute Stereochemistry of compound V was determined using single crystal X-ray diffraction. X-ray diffraction was recorded on a Bruker AXS™ X8 PROTEUM system. The data have been processed using APEX II suite from Bruker AXS™. Absolute stereochemistry of compounds VI, VIII, IX, XI, XII, XIV, XV, XVII, XVIII, XX and XXI were determined by comparing their circular dichroism spectra with that of compound IV. These spectra were recorded on a Jasco J-815 CD spectrometer.

Compounds IV, V, VI, VII, VIII, IX, X, XI, XII, XVI, XVII, XVIII, XIX, XX, and XXI were found to have the following general formula (2):

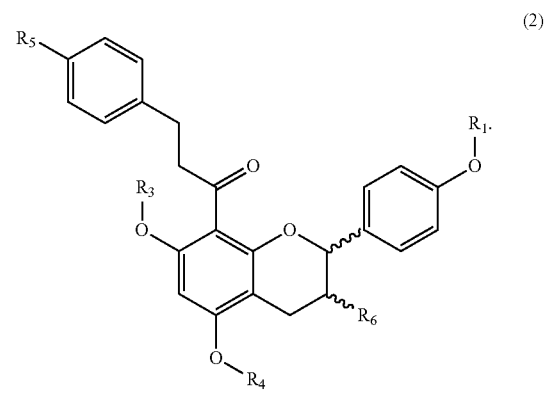

| Compound | $R_1$ | $R_4$ | $R_3$ | $R_5$ | $R_6$ | Stereochemistry |
|---|---|---|---|---|---|---|
| IV | H | H | H | H | H | Racemic; |
| V | H | H | H | H | H | 2S; |
| VI | H | H | H | H | H | 2R; |
| VII | H | H | H | —O—CH$_3$ | H | Racemic; |
| VIII | H | H | H | —O—CH$_3$ | H | 2S; |
| IX | H | H | H | —O—CH$_3$ | H | 2R; |
| X | H | CH$_3$ | H | OH | H | Racemic; |
| XI | H | CH$_3$ | H | OH | H | 2S; |
| XII | H | CH$_3$ | H | OH | H | 2R; |
| XVI | H | H | H | H | OH | Racemic; |
| XVII | H | H | H | H | OH | 2R,3S; |
| XVIII | H | H | H | H | OH | 2S,3R; |
| XIX | H | H | H | —O—CH$_3$ | OH | Racemic; |
| XX | H | H | H | —O—CH$_3$ | OH | 2R,3S; or |
| XXI | H | H | H | —O—CH$_3$ | OH | 2S,3R. |

Compounds XIII, XIV and XV were found to have the following general formula (3):

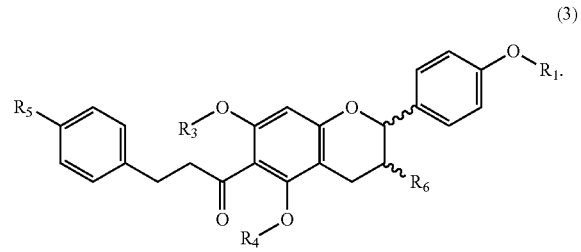

| Compound | $R_1$ | $R_3$ | $R_4$ | $R_5$ | $R_6$ | Stereochemistry |
|---|---|---|---|---|---|---|
| XIII | H | H | H | H | OH | Racemic; |
| XIV | H | H | H | H | OH | 2R,3S; or |
| XV | H | H | H | H | OH | 2S,3R |

Materials and Methods

Bacteria Strains. All bacteria were provided by the Centre de santé et services sociaux de Chicoutimi, complexe hospitalier de la Sagamie. The *S. aureus* wild type strain was from ATCC (ATCC 25923).

Antibiotic agents. Gentamicin sulfate was provided by Calbiochem. Chloramphenicol was provided by Sigma-Aldrich.

Antibiotic assay. The antibiotic assays were performed in 96-well plates (BD Falcon). The bacteria strains were inoculated in nutrients broth. All bacteria strains were dosed by spectrophotometry at 660 nm where 1 D.O=$2\times10^8$ bacteria/mL. All bacteria were plated in nutrients broth at a concentration of 450 000 bacteria/m L.

Compounds IV to XXI were diluted in dimethylsulfoxide. The solvent concentration was 0.25%, which was not toxic for the bacteria. The compounds were tested at 8 different concentrations.

Each well contained: 100 μL of bacteria, 100 μL of the compounds tested. The plates were incubated at 37° C. for 6 h. The absorption was read using a Varioskan flash multimode Reader™ (Thermo Scientific) at 660 nm.

Cytotoxicity assay. The cytotoxicity assay was performed in 96-well plates (BD Falcon). The WS-1 cell lines were provided by ATCC. The WS-1 was cultured in DMEM+10% fetal calf serum. The cells were plated in a volume of 100 μL at a density of 5000 cells per well and incubated at 37° C.+5% $CO_2$ for 24 h to promote cell adhesion.

The compounds tested were then added at 8 different concentrations. The plates were incubated at 37° C.+5% $CO_2$ for 48 h. The cells were then washed with 100 μL of HBSS and 150 μL of a 2% resazurin were added to the wells. The plates were again incubated at 37° C.+5% $CO_2$ for 1 h and their fluorescence was read using a Fluoroskan Ascent™ FL (thermo) using an excitation wavelength of 530 nm and an emission wavelength of 590 nm.

Antibiotic Activity and Cytotoxicity Against MRSA Strains

MRSA. Ten (10) strains of MRSA obtained as described above were tested along with an S. aureus wild type (WT) strain (ATCC 25923). Table 6 shows that Compounds IV to XXI had a similar MIC for MRSA and for S. aureus WT. This indicates that the MRSA strains are not resistant to these compounds.

TABLE 6

Antibiotic activity of compounds IV to XXI against 10 MRSA strains and against S. aureus wild type strain (ATCC 25923). MIC values are shown along their standard error. All values are in μM.[a]

| | MRSA | | | | | |
|---|---|---|---|---|---|---|
| Comp. | 1 | 2 | 3 | 4 | 5 | 6 |
| IV | 0.84 ± 0.04 | 1.50 ± 0.06 | 1.02 ± 0.06 | 2.6 ± 0.2 | 0.95 ± 0.01 | 2.11 ± 0.07 |
| V | 4.1 ± 0.1 | 2.58 ± 0.10 | 3.8 ± 0.2 | 4.7 ± 0.4 | 4.4 ± 0.1 | 6.9 ± 0.4 |
| VI | 3.5 ± 0.1 | 2.9 ± 0.2 | 3.8 ± 0.3 | 5.2 ± 0.4 | 4.9 ± 0.6 | 14.2 ± 0.9 |
| VII | 2.9 ± 0.1 | 2.5 ± 0.1 | 1.7 ± 0.1 | 2.4 ± 0.2 | 2.0 ± 0.1 | 2.7 ± 0.1 |
| VIII | >50 | >50 | >50 | >50 | >50 | >50 |
| IX | 7.7 ± 0.3 | 9 ± 1 | 6.25 ± 0.06 | 6.7 ± 0.2 | 6.9 ± 0.4 | 7.1 ± 0.9 |
| X | 5.2 ± 0.4 | 5.7 ± 0.4 | 4 | 3 | 4 ± 2 | 9 ± 1 |
| XI | <0.39 | <0.39 | <0.39 | <0.39 | <0.39 | <0.39 |
| XII | 0.55 ± 0.07 | 0.65 ± 0.03 | 1.10 ± 0.07 | 0.64 ± 0.02 | 0.60 ± 0.01 | 0.76 ± 0.04 |
| XIII | 2.9 ± 0.2 | 2.7 ± 0.1 | 7.8 ± 0.5 | 6.8 ± 0.7 | 2.7 ± 0.3 | 5.4 ± 0.4 |
| XIV | 21.9 ± 0.2 | 25 ± 2 | 18 ± 1 | 22 ± 2 | 20 ± 2 | 20 ± 3 |
| XV | 24.3 ± 0.9 | 27 ± 1 | 29 ± 3 | 22 ± 2 | 18 ± 2 | 18.9 ± 0.4 |
| XVI | 5.6 ± 0.5 | 4.7 ± 0.4 | 5.1 ± 0.3 | 5.7 ± 0.4 | 4.1 ± 0.6 | 5.4 ± 0.7 |
| XVII | 13 ± 1 | 12 ± 1 | 16.7 ± 0.5 | 15 ± 1 | 5.1 ± 0.2 | 6 ± 2 |
| XVIII | 12 ± 1 | 14 ± 1 | 15.9 ± 0.8 | 15 ± 1 | 11.5 ± 0.4 | 11 ± 2 |
| XIX | 2.6 ± 0.1 | 2.4 ± 0.1 | 4.3 ± 0.4 | 2.9 ± 0.6 | 3.1 ± 0.6 | 2.8 ± 0.2 |
| XX | 14 ± 1 | 11.4 ± 0.5 | 8.9 ± 0.3 | 7.6 ± 0.2 | 3.8 ± 0.3 | 11.2 ± 1.0 |
| XXI | 17 ± 2 | 7 ± 2 | 8.5 ± 0.6 | 12.3 ± 0.5 | 7.7 ± 0.6 | 12 ± 1 |

| | MRSA | | | | S. aureus |
|---|---|---|---|---|---|
| Comp. | 7 | 8 | 9 | 10 | WT |
| IV | 1.22 ± 0.04 | 1.35 ± 0.05 | 1.32 ± 0.04 | 1.23 ± 0.08 | 1.27 ± 0.06 |
| V | 3.0 ± 0.2 | 3.8 ± 0.4 | 6.2 ± 0.4 | 5.0 ± 0.3 | 2.5 ± 0.2 |
| VI | 3.4 ± 0.2 | 3.8 ± 0.3 | 4.7 ± 0.2 | 4.65 ± 0.06 | 2.7 ± 0.3 |
| VII | 2.13 ± 0.02 | 2.2 ± 0.5 | 2.5 ± 0.2 | 1.2 ± 0.2 | 2.2 ± 0.2 |
| VIII | >50 | >50 | >50 | >50 | >50 |
| IX | 5.2 ± 0.4 | 4.9 ± 0.2 | 3.7 ± 0.2 | 7.5 ± 0.7 | 8.0 ± 0.3 |
| X | 5.3 ± 0.2 | 5.3 ± 0..5 | 5.3 ± 0.4 | 5.6 ± 0.5 | 5.3 ± 0.6 |
| XI | <0.39 | <0.39 | <0.39 | <0.39 | <0.39 |
| XII | 0.57 ± 0.06 | 0.641 ± 0.01 | 0.86 ± 0.03 | 0.7 ± 0.1 | 0.58 ± 0.02 |
| XIII | 2.0 ± 0.2 | 3.4 ± 0.3 | 2.9 ± 0.1 | 4.2 ± 0.8 | 3.2 ± 0.2 |
| XIV | 18.5 ± 0.4 | 23.4 ± 1.0 | 20 ± 2 | 11.4 ± 0.6 | 10.9 ± 0.6 |
| XV | 20 ± 1 | 17 ± 2 | 30 ± 1 | 7.8 ± 0.3 | 13 ± 1 |
| XVI | 3.5 ± 0.3 | 5.3 ± 0.6 | 4.8 ± 0.2 | 3.3 ± 0.1 | 5.9 ± 0.3 |
| XVII | 8.2 ± 0.7 | 10.2 ± 0.8 | 17 ± 1 | 17 ± 1 | 13.0 ± 0.8 |
| XVIII | 7.5 ± 0.4 | 9.5 ± 1.0 | 13 ± 2 | 12 ± 1 | 9.9 ± 0.7 |
| XIX | 2.6 ± 0.1 | 2.7 ± 0.2 | 3.0 ± 0.3 | 2.56 ± 0.04 | 2.5 ± 0.1 |
| XX | 12.1 ± 0.7 | 7.0 ± 1.0 | 12 ± 1 | 12.6 ± 0.3 | 14.0 ± 0.8 |
| XXI | 11.4 ± 0.5 | 8.2 ± 0.2 | 10.8 ± 0.8 | 12 ± 1 | 28 ± 2 |

[a]Gentamicin and chloramphenicol were also tested as controls. The values obtained were greater than 2.5 μM for Chloramphenicol and smaller than 1.56 μM for gentamicin and are not reported.

Therapeutic Index

The therapeutic index is the ratio between the toxicity on normal cells, in this case fibroblast, and the toxicity on bacteria. In Table 7, the therapeutic indexes of compounds IV to XXI are presented.

TABLE 7

Therapeutic indexes of compounds IV to XXI

| Compound | WS-1 | S. aureus WT ATCC 25923 | Therapeutic index |
|---|---|---|---|
| IV | 16 ± 2 | 1.27 ± 0.06 | 12 |
| V | >50 | 2.5 ± 0.2 | 20 |
| VI | >50 | 2.7 ± 0.3 | 18 |
| VII | 26 | 2.2 ± 0.2 | 11 |
| VIII | >50 | >50 | 1 |
| IX | >50 | 8.0 ± 0.3 | 6 |
| X | 16 ± 4 | 5.3 ± 0.6 | 3 |
| XI | >50 | <0.39 | 128 |
| XII | >50 | 0.58 ± 0.02 | 86 |
| XIII | 10.1 ± 0.8 | 3.2 ± 0.2 | 3 |
| XIV | >50 | 10.9 ± 0.6 | 4 |
| XV | >50 | 13 ± 1 | 3 |
| XVI | >50 | 5.9 ± 0.3 | 8 |
| XVII | >50 | 13.0 ± 0.8 | 3 |
| XVIII | >50 | 9.9 ± 0.7 | 5 |
| XIX | 8.2 ± 1.0 | 2.5 ± 0.1 | 3 |
| XX | >50 | 14.0 ± 0.8 | 3 |
| XXI | >50 | 28 ± 2 | 1 |

Example 3

Preparation of a *Populus Balsamifera* Bud Extracts and of Fractions Thereof

Buds from different trees of *Populus balsamifera* were collected in March 2005 at longitude 71°2' west and latitude 48°23' north near Chicoutimi, Québec province, Canada. The plant was authenticated by Mr. Patrick Nadeau (Université du Québec à Chicoutimi) and a voucher specimen (No. 499678) was deposited at the Louis-Marie Herbarium of Université Laval, Québec City, Canada. After collection, buds were kept frozen until extraction.
1. Coarse grinding was executed using an electrical blender on buds previously immersed in liquid nitrogen.
2. The resulting crude powder (1036 g) was extracted 5 times (5 h each time) with 2.5 L of 95% EtOH under reflux and extracts were combined.
3. After evaporation of the EtOH solvent using a rotary evaporator, the residue was suspended in MeOH and extracted with hexanes.
4. The dried MeOH residue (380.4 g) was suspended in $Et_2O$ and extracted with water.
5. The dried $Et_2O$ phase (355.1 g) was submitted to silica gel column chromatography ($CHCl_3$-MeOH, 40:1-20:1-10:1-0:1, v:v) yielding 7 fractions named fraction A, B, C, D, E, F and G (FIG. 1).
6. Fraction F was submitted to silica gel column chromatography ($CHCl_3$-MeOH, 40:1-30:1-20:1-10:1-0:1, v:v) affording 6 fractions named fraction F1, F2, F3, F4, F5 and F6 (FIG. 1).

Example 4

Characterization of *Populus Balsamifera* Bud Extracts and of Fractions Thereof-Thin Layer Chromatography Thin layer chromatography conditions. Thin layer chromatography (TLC) was carried out on silica gel glass plates (40-63 μm with $F_{254}$ indicator) supplied by Silicycle Inc. (Ville de Québec, Québec, Canada). Elution was conducted in a 15:1 $CHCl_3$-MeOH mixture and visualized under UV 254 nm for I and under UV 365 nm after treatment with 1% methanolic diphenylboryloxyethylamine (NP) followed by 5% polyethylene glycol-4000 (PEG) for II.

Figure 5:
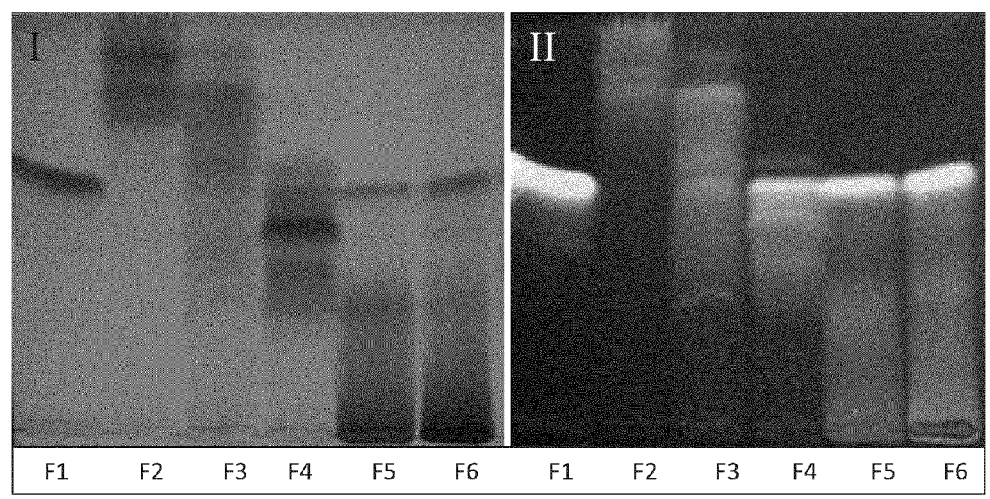
FIG. 5 shows the thin layer chromatograms obtained from fractions F1, F2, F3, F4, F5 and F6. Elution was conducted in 15:1 CHCl$_3$-MeOH mixture and visualized under UV 254 nm (I) and under UV 365 nm after treatment with 1% methanolic diphenylboryloxyethylamine (NP) followed by 5% polyethylene glycol-4000 (PEG) (II)
Figure 6:
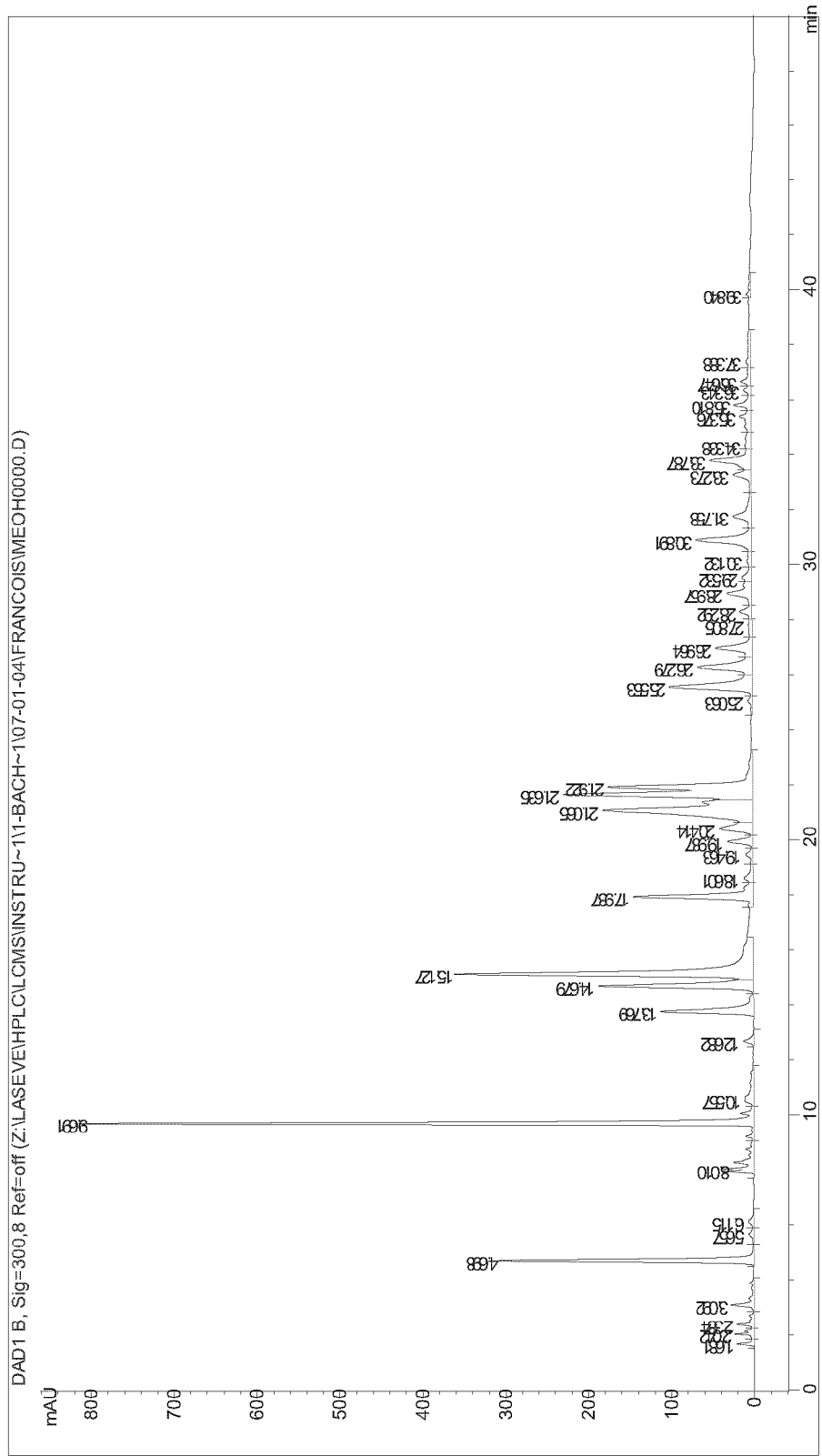
FIG. 6 shows the HPLC chromatogram obtained from the methanol soluble fraction obtained from the *Populus Balsamifera* buds ethanolic extract of FIG. 2.
Figure 7:
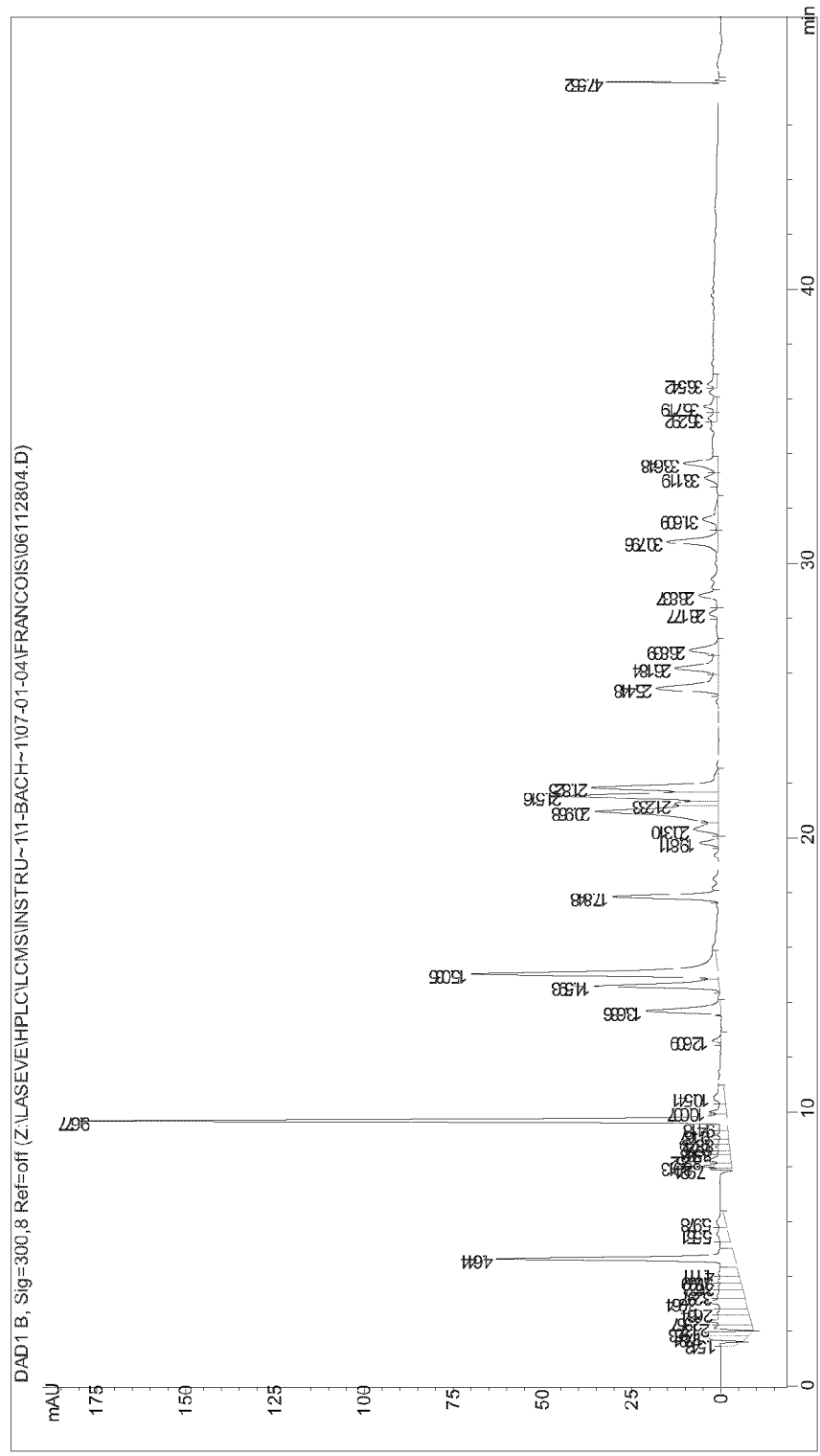
FIG. 7 shows the HPLC chromatogram obtained from the diethyl ether soluble fraction of FIG. 3.
Figure 8:
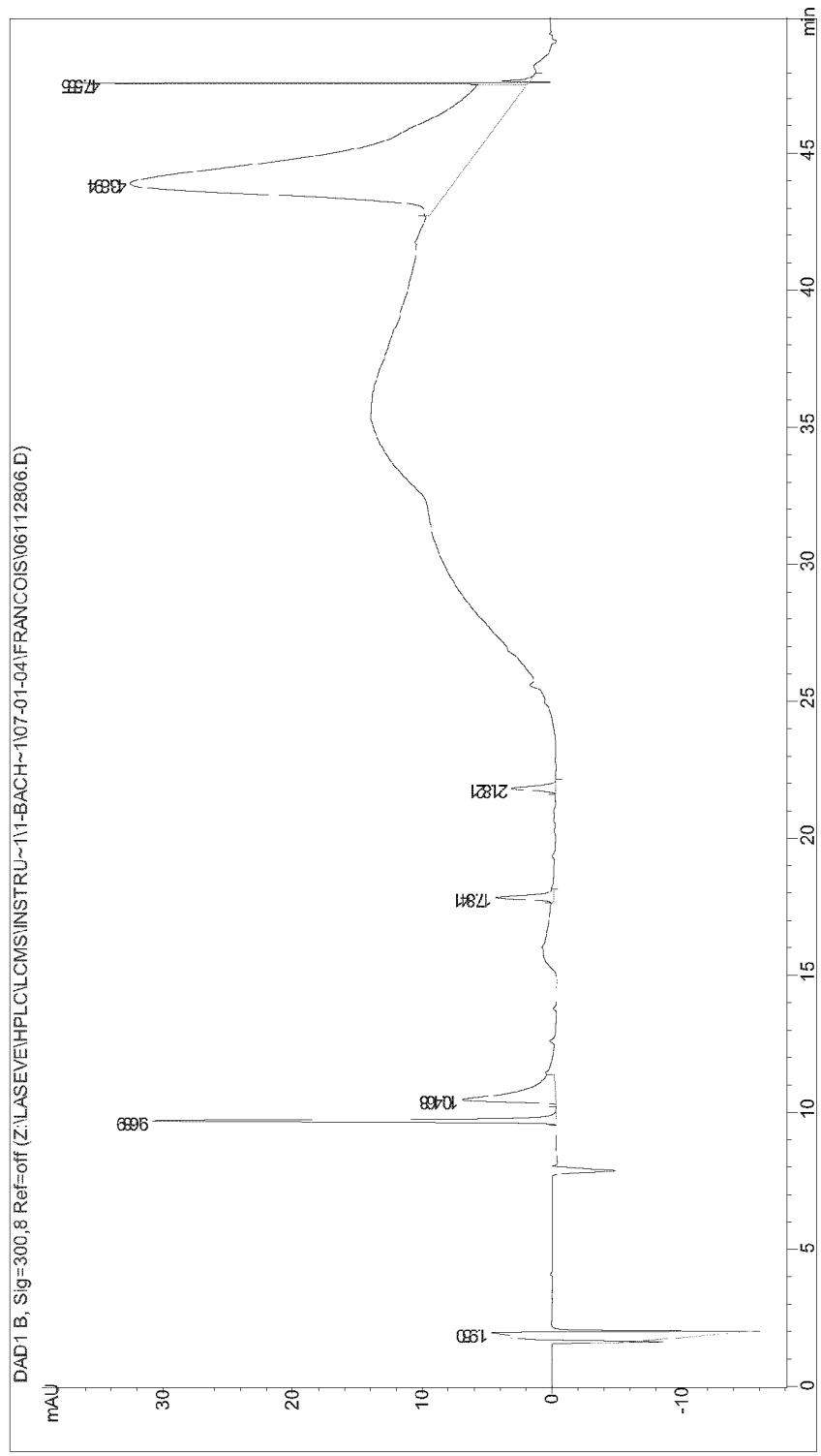
FIG. 8 shows the HPLC chromatogram obtained from fraction A.
Figure 9:
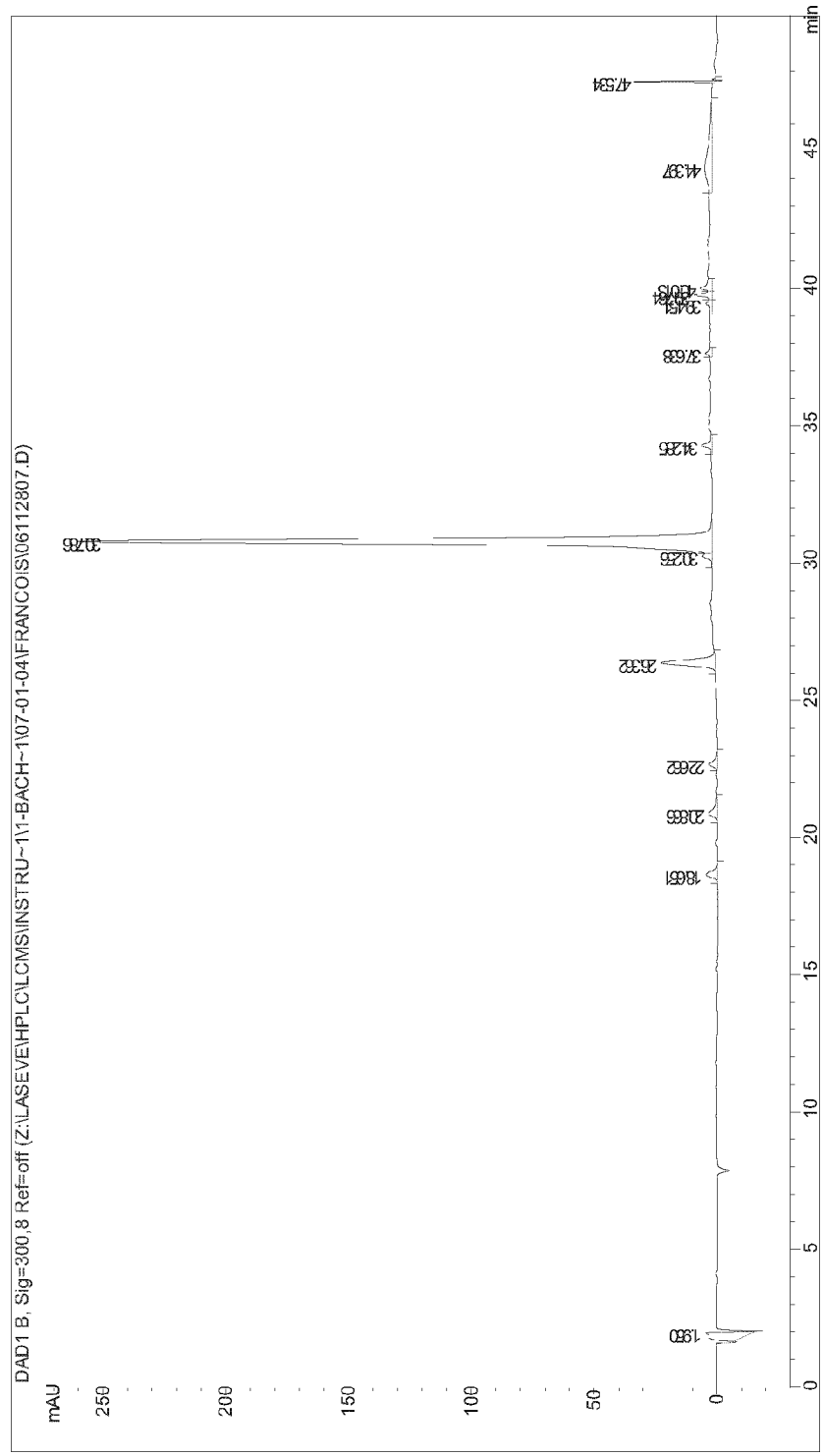
FIG. 9 shows the HPLC chromatogram obtained from fraction B of FIG. 4.
Figure 10:
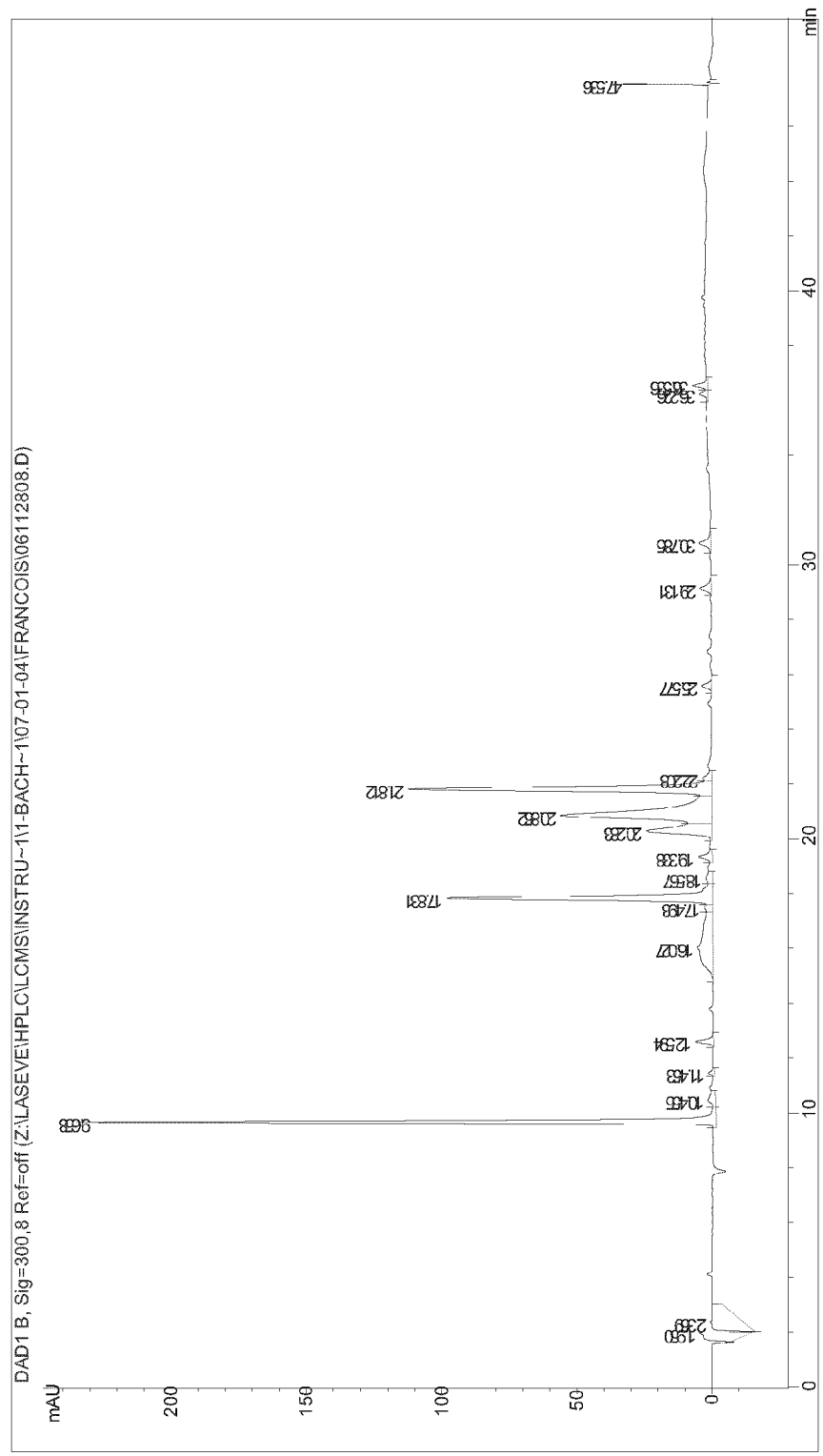
FIG. 10 shows the HPLC chromatogram obtained from fraction C of FIG. 4.
Figure 11:
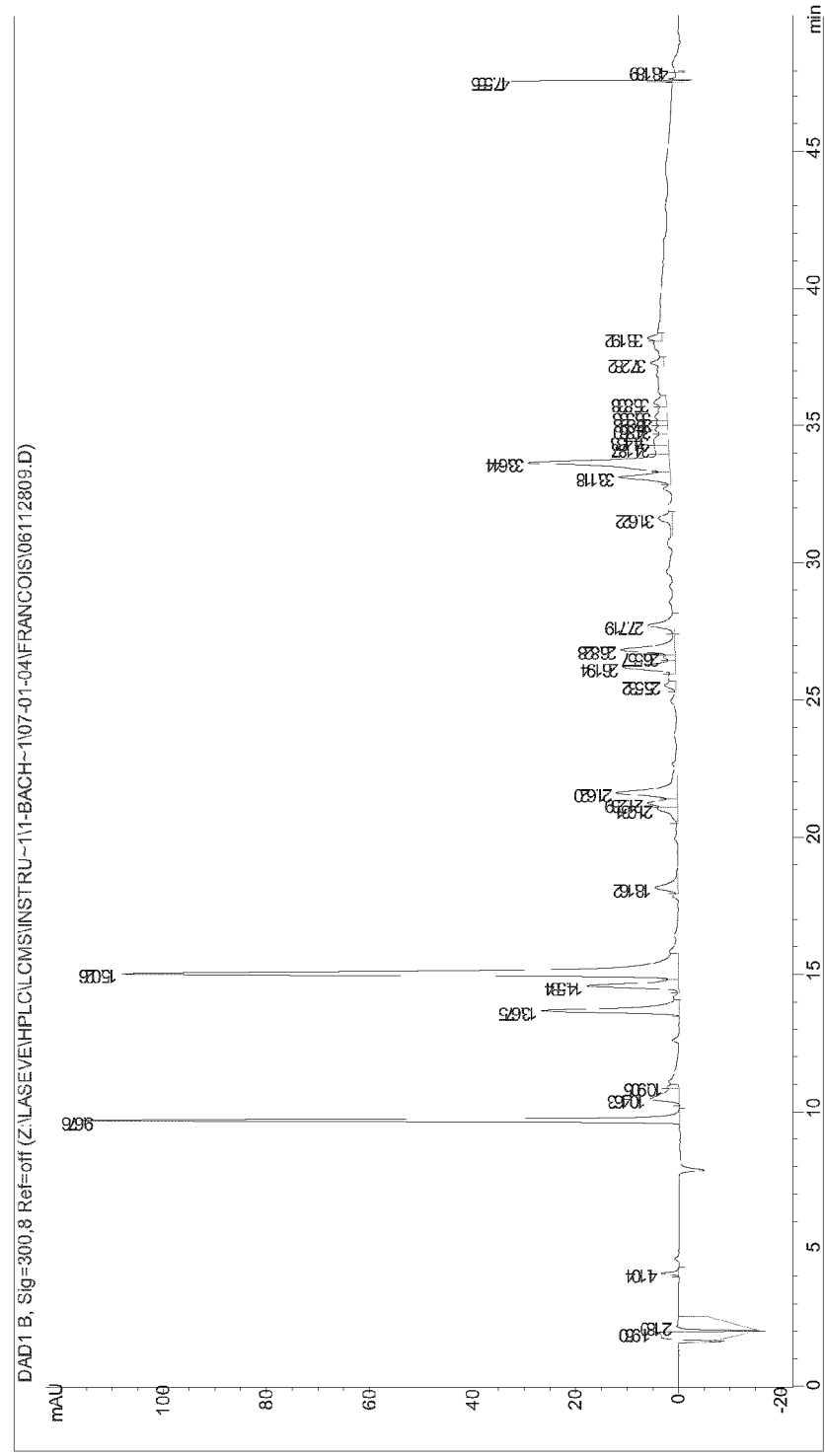
FIG. 11 shows the HPLC chromatogram obtained from fraction D of FIG. 4.
Figure 12:
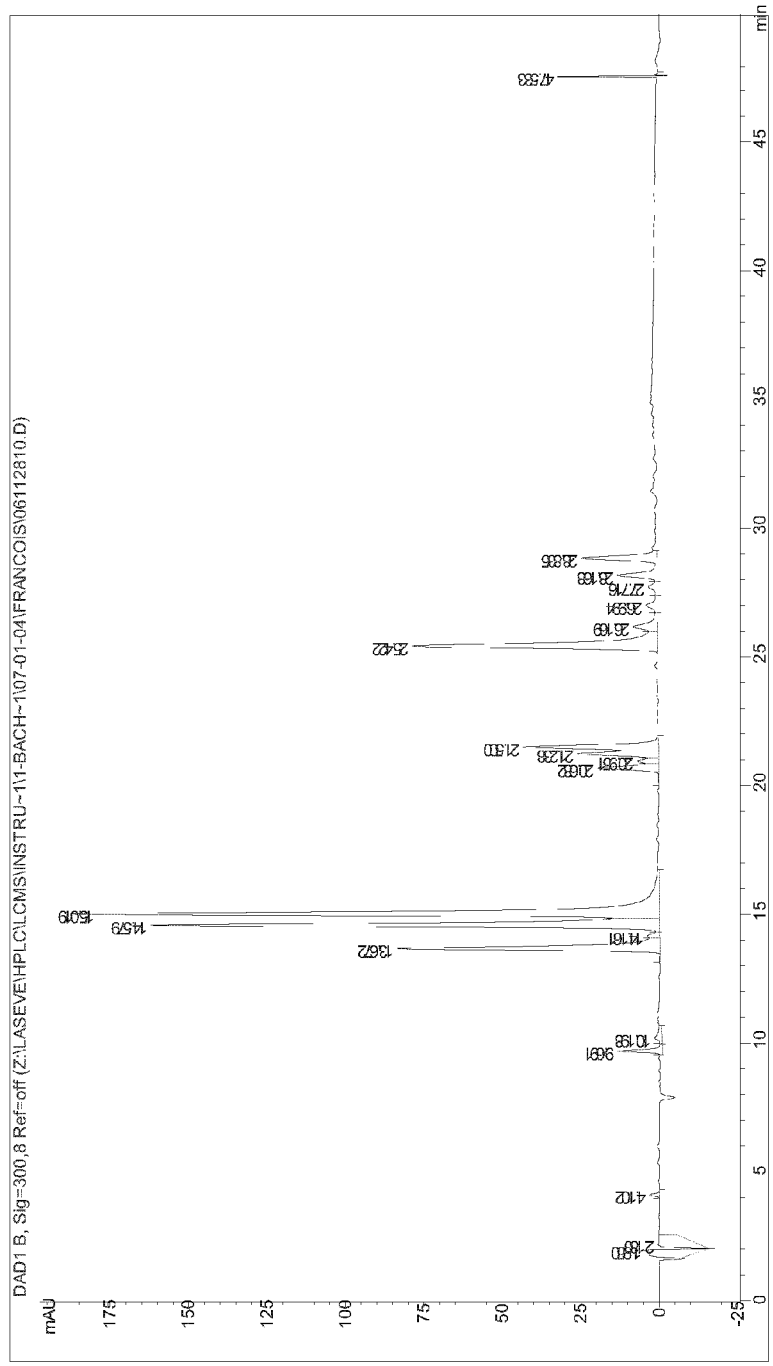
FIG. 12 shows the HPLC chromatogram obtained from fraction E of FIG. 4.
Figure 13:
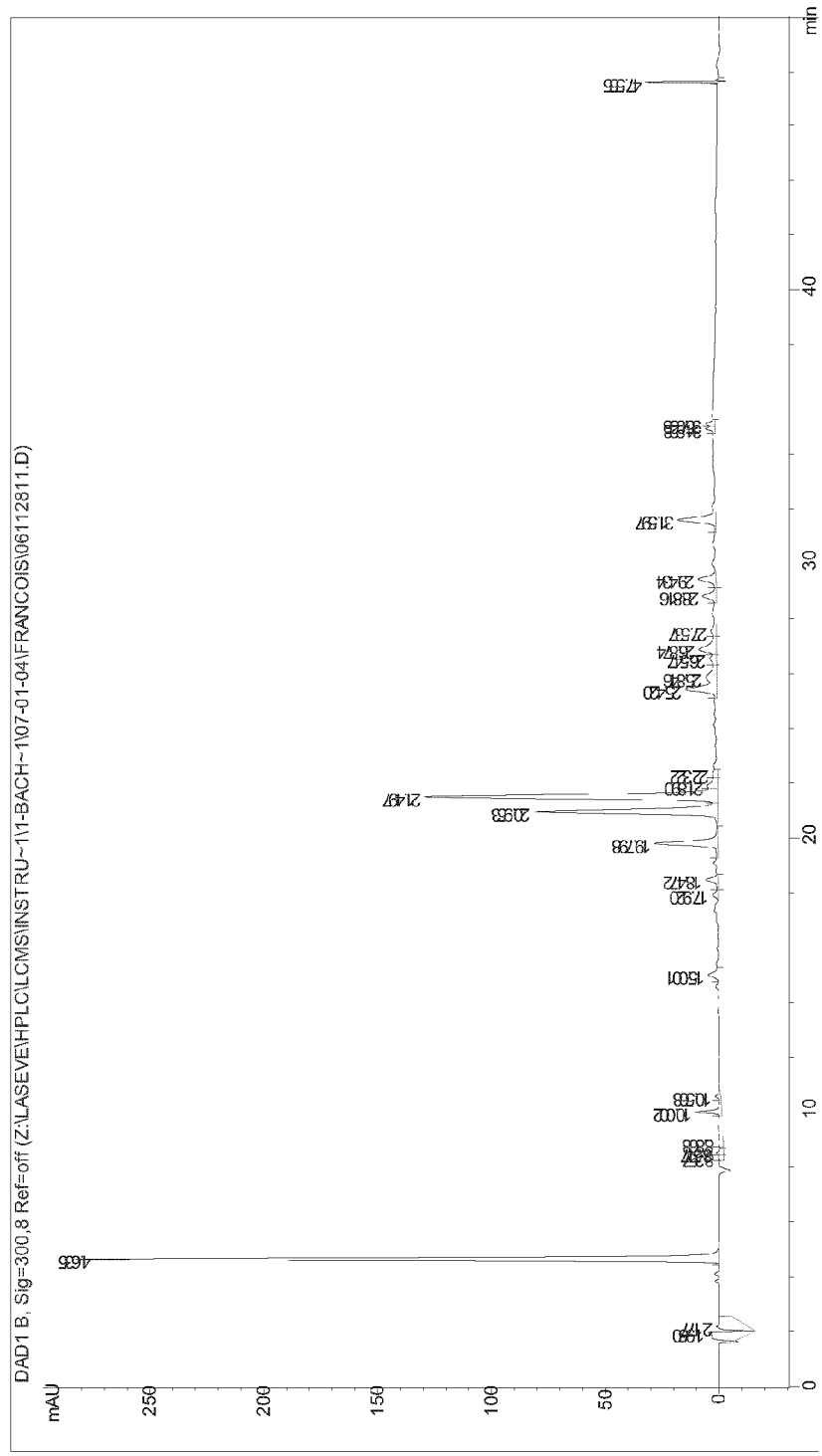
FIG. 13 shows the HPLC chromatogram obtained from fraction F of FIG. 4.
Figure 14:
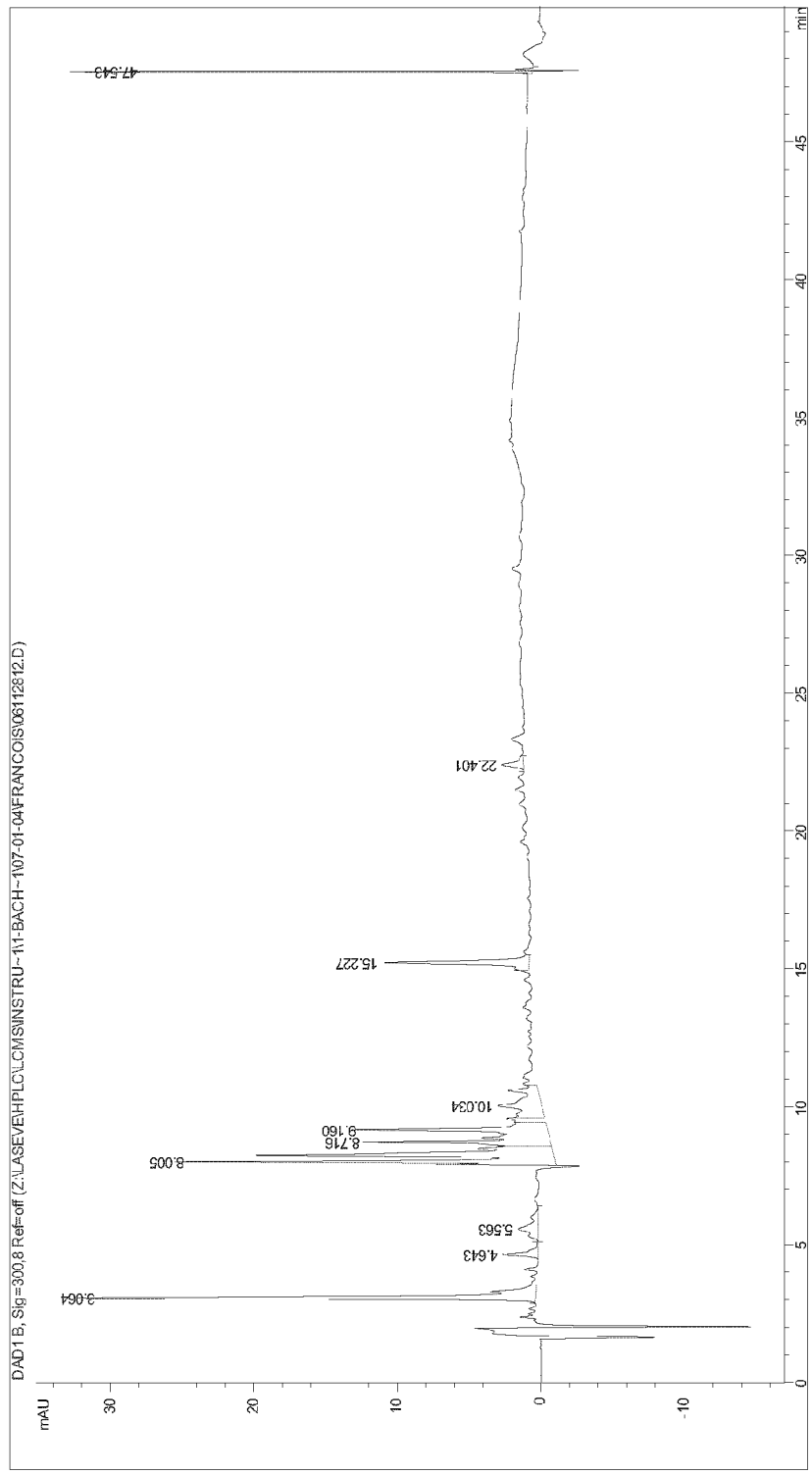
FIG. 14 shows the HPLC chromatogram obtained from fraction G.
Figure 15:
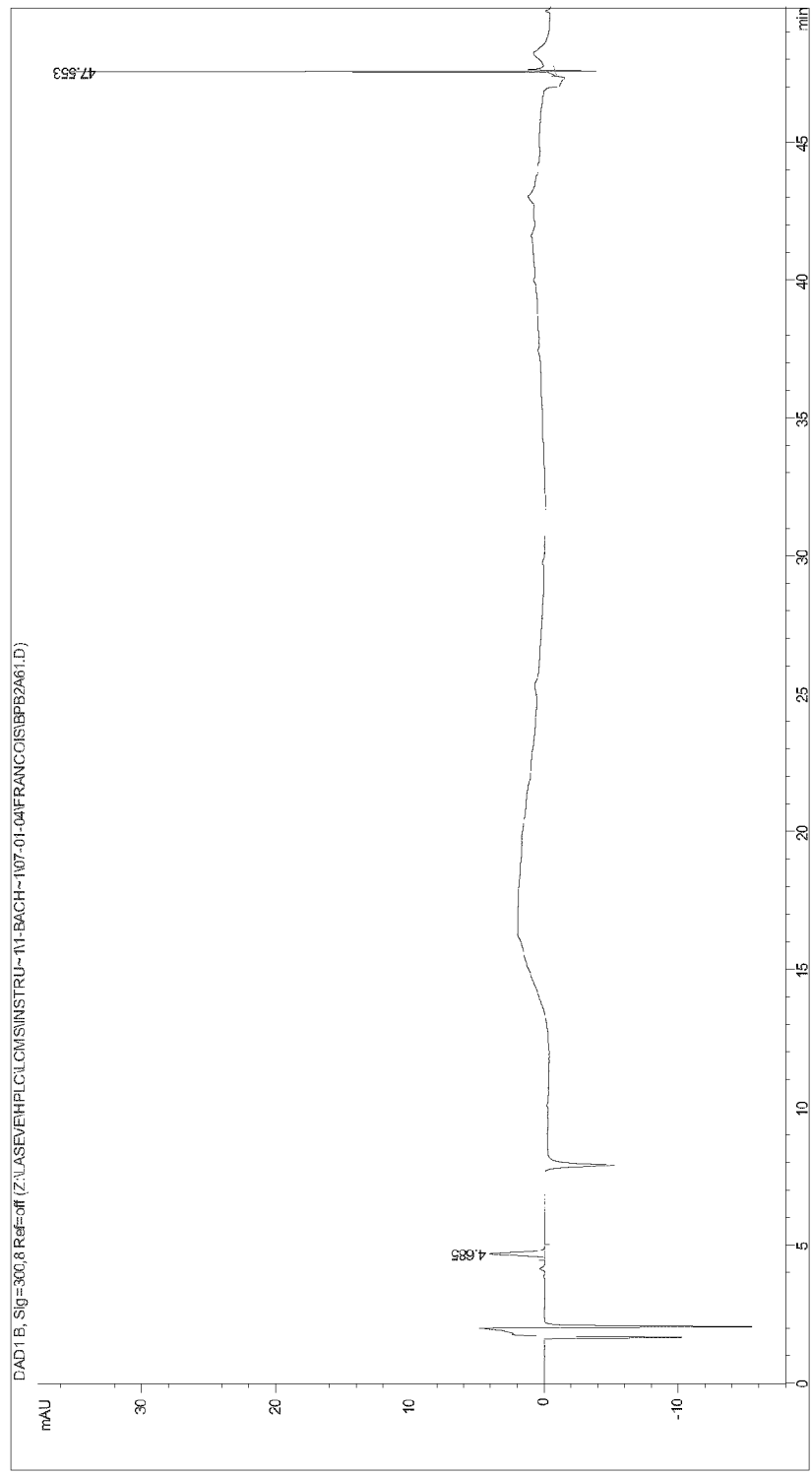
FIG. 15 shows the HPLC chromatogram obtained for fraction F1 of FIG. 5.
Figure 16:
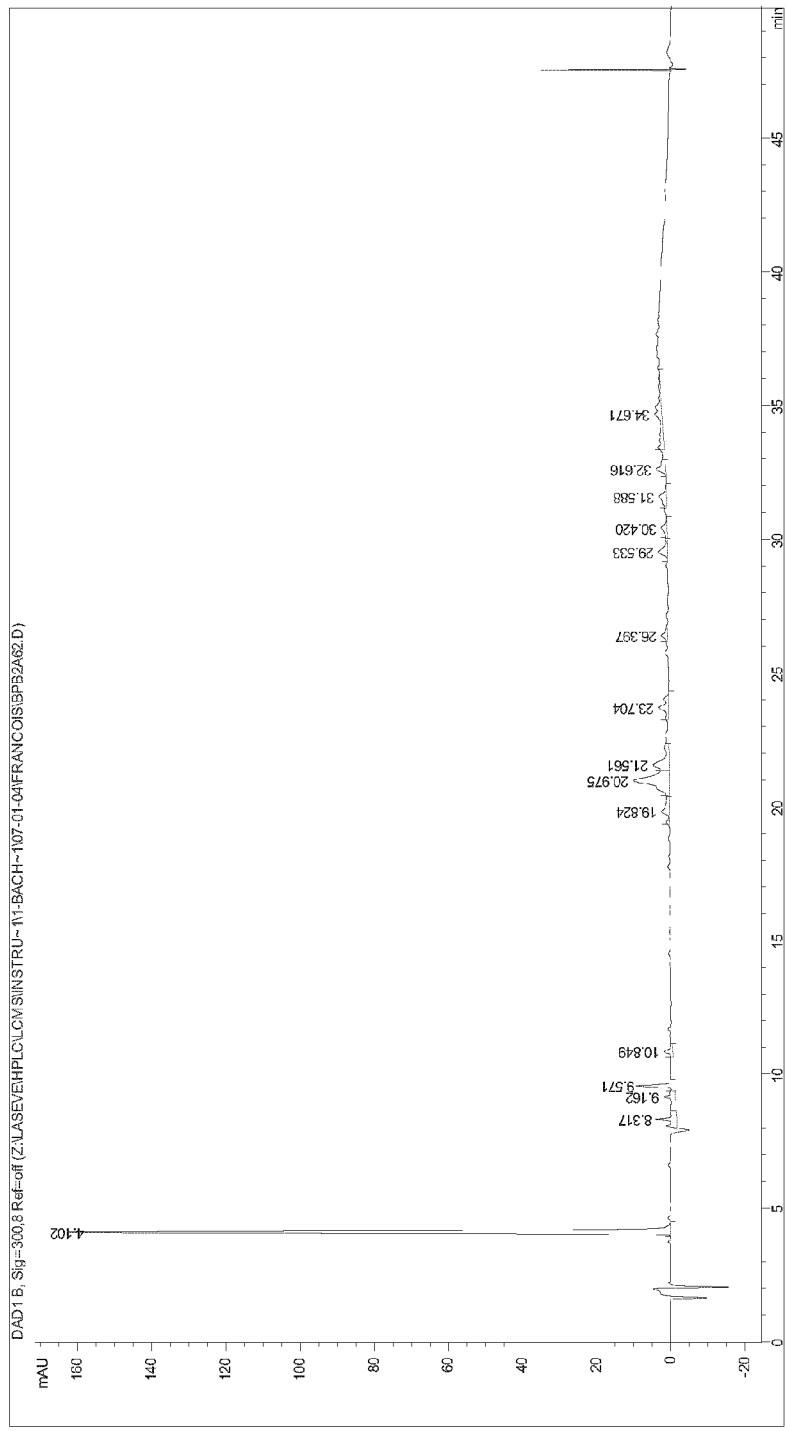
FIG. 16 shows the HPLC chromatogram obtained for fraction F2 of FIG. 5.
Figure 17:
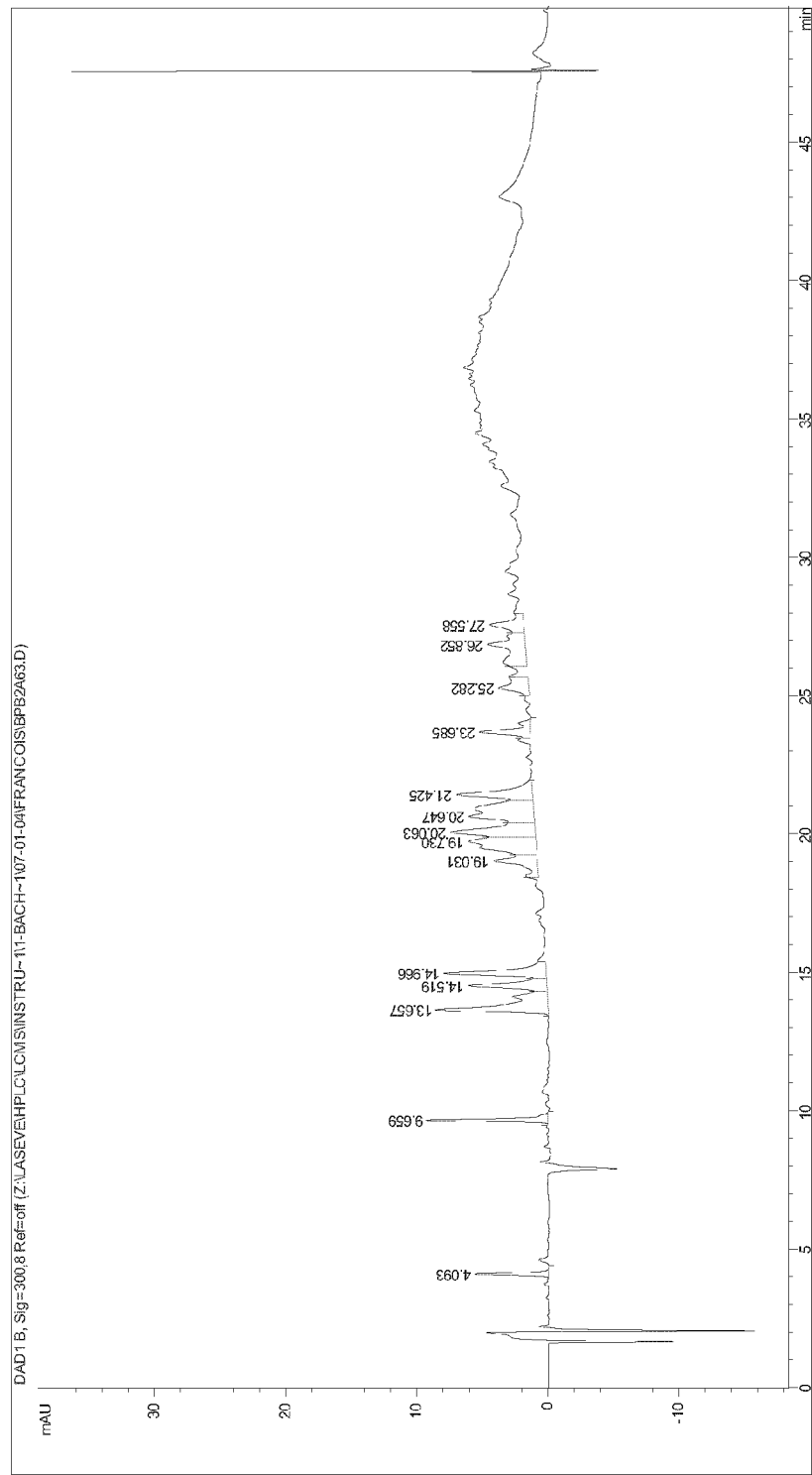
FIG. 17 shows the HPLC chromatogram obtained for fraction F3 of FIG. 5.
Figure 18:
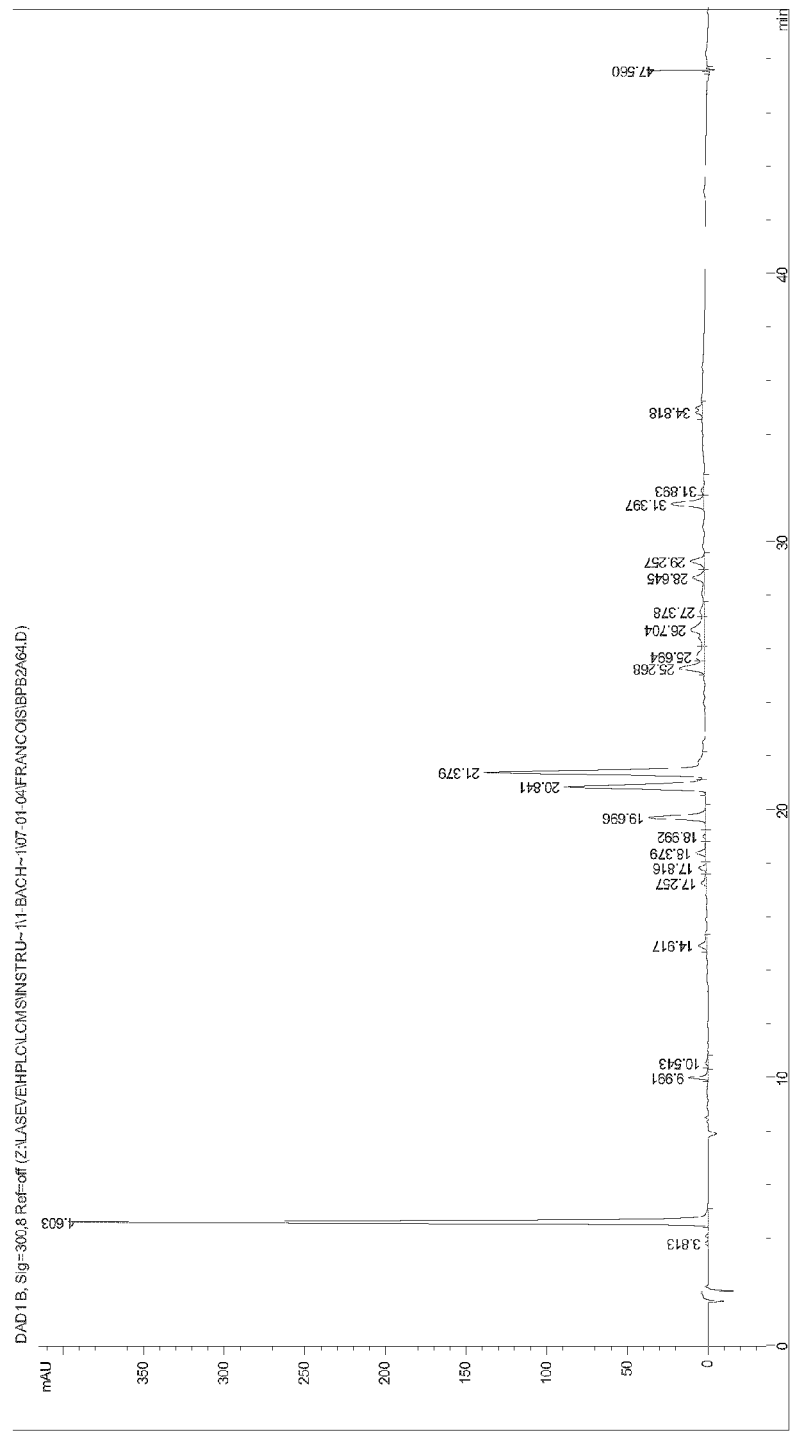
FIG. 18 shows the HPLC chromatogram obtained for fraction F4 of FIG. 5.
Figure 19:
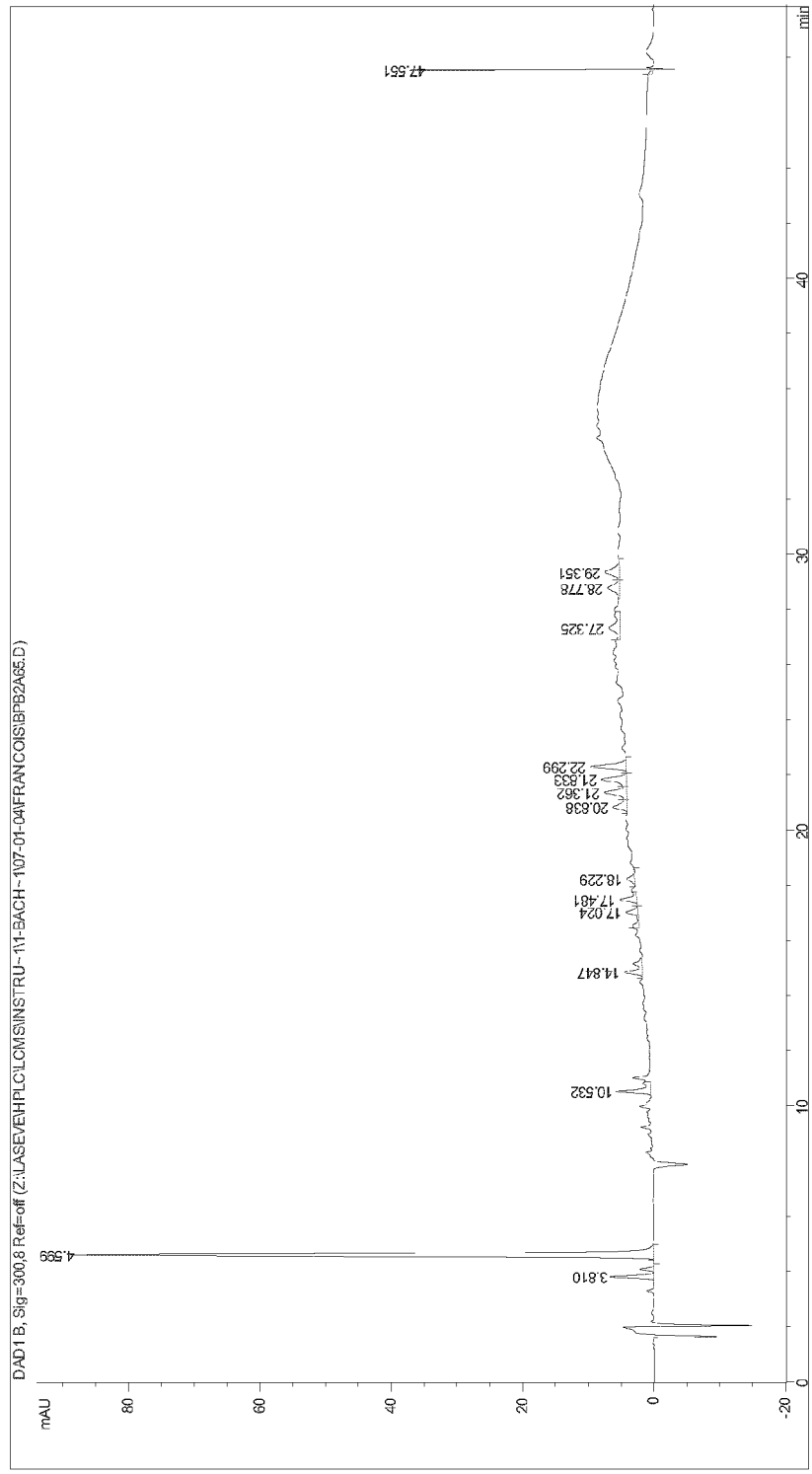
FIG. 19 shows the HPLC chromatogram obtained for fraction F5 of FIG. 5.
Figure 20:
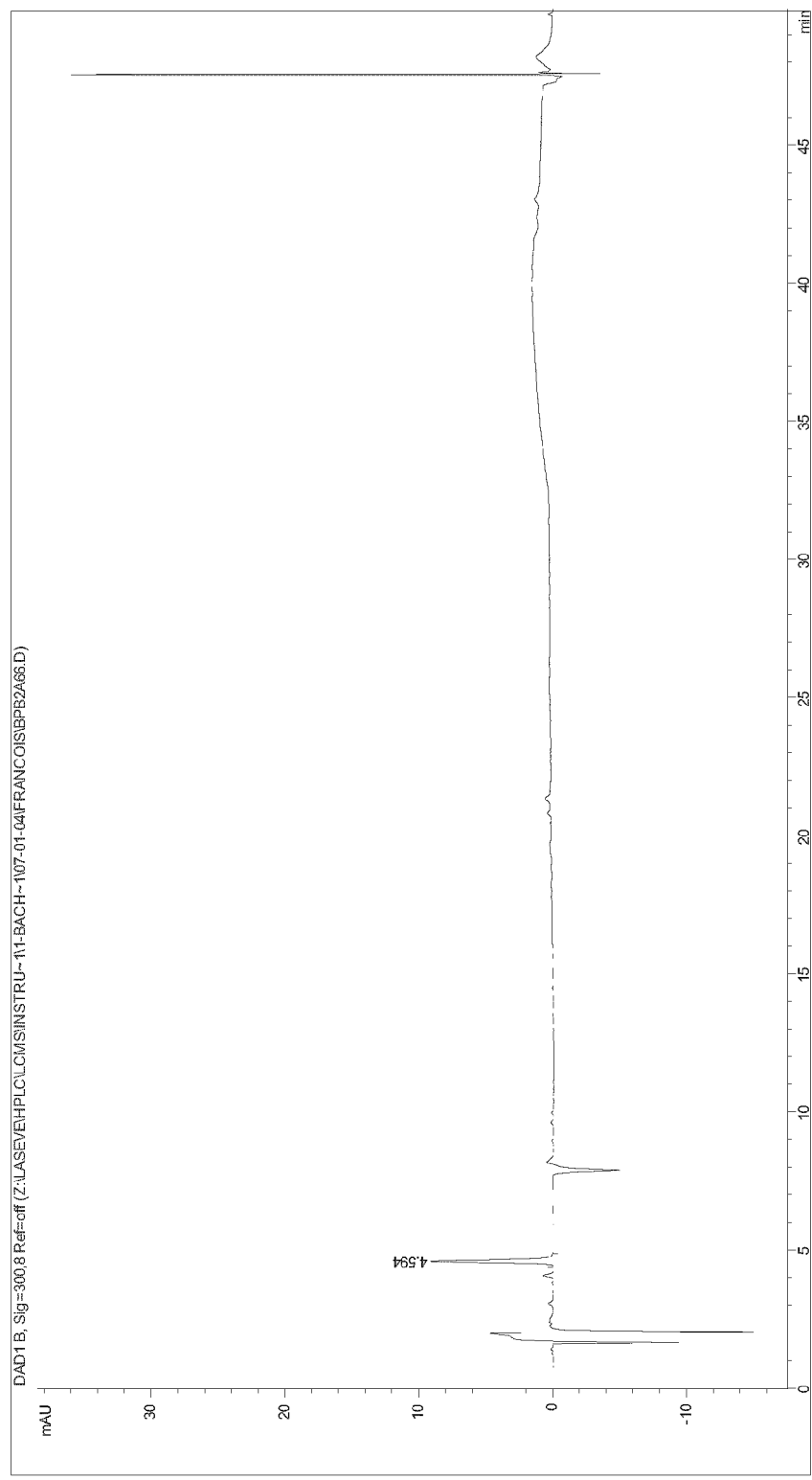
FIG. 20 shows the HPLC chromatogram obtained for fraction F6 of FIG. 5.

FIGS. 2, 3, 4, and 5 show the thin layer chromatograms obtained for the buds ethanolic extract and the methanol soluble and hexane soluble fractions (FIG. 2), the diethyl ether soluble and water soluble fractions (FIG. 3), fractions B, C, D, E and F (FIG. 4), and fractions F1, F2, F3, F4, F5 and F6 (FIG. 5).

Example 5

Characterization of *Populus Balsamifera* Bud Extracts and of Fractions Thereof-HPLC HPLC method. The instrumentation used for HPLC analysis consisted of an Agilent™ 1100 series with a UV-MSD detector. Control of the equipment, data acquisition, processing and management of chromatographic information were performed with the Chemstation™ software (Agilent). The analytical HPLC separations were conducted on an Inertsil™ Prep-ODS column (5 μm, 4.6×150 mm) from GL Sciences Inc. (Tokyo, Japan). Solvents were water containing 0.1% formic acid (solvent A) and acetonitrile containing 0.1% formic acid (solvent B). The gradient elution was carried out as follows: Solvent B remained at 20% for 5 min, was immediately increased to 35% and then gradually increased to 60% in 25 min. Finally, solvent B was gradually increased to 100% in 10 min and maintain there for another 10 min. The flow rate was 1 ml/min and the UV absorbance was monitored at 300 nm with a bandwidth of 8 nm. FIGS. 6 to 20 show the HPLC chromatograms obtained for the various extracts and fractions.

Example 6

Antibiotic Activity of *Populus Balsamifera* Bud Extracts and of Fractions Thereof-HPLC Bacteria Strain. The *S. aureus* wild type strain was from ATCC (ATCC 25923), the *E. coli* was obtained from ATCC (ATCC 25922) and MRSA 1, 2 and 3 were obtained as described above.

Antibiotic agents. Gentamicin sulfate was provided by Calbiochem.

The antibiotic assays were performed in 96-well plates (BD Falcon). The bacteria strains were inoculated in Nutrient Broth (BD) for the gram negative bacteria (e.g., *E. coli*) and Tryptic soy broth (BD) with 10% of defibrinated sheep blood (PML microbiological) for gram positive strain (e.g., *S. aureus* WT AATCC 25923 and MRSAs 1, 2 and 3). All bacteria strains were dosed by spectrophotometry at 660 nm where 1 D.O=2×108 bacteria/mL. All bacteria were plated in their respective broth at a concentration of 450 000 bacteria/mL.

The extract and fractions were diluted in dimethyl sulfoxide and the above-noted antibiotic agents were diluted in water. The solvent concentration was 0.25%, which was not toxic for the bacteria. The extract, the fractions and the above-noted antibiotic agents were tested at 8 different concentrations.

Each well contained: 100 μL of bacteria, 50 μL of the compounds tested (the extract, the fractions and the above-noted antibiotic agent) and 50 μL of a 4% resazurin (Sigma) solution. The plates were incubated at 37° C. for 5 h. The fluorescence was read using a Fluoroskan Ascent™ FL (thermo) using an excitation wavelength of 530 nm and an emission wavelength of 590 nm.

Cytotoxicity assay. The cytotoxicity assay was performed in 96-well plates (BD Falcon). The WS-1 cell lines were provided by ATCC. The WS-1 was cultured in DMEM+10% fetal calf serum. The cells were plated in a volume of 100 μL at a density of 5000 cells per well and incubated at 37° C.+5% CO2 for 24 h to promote cell adhesion.

The extracts, fractions and the above-noted control antibiotic agent were then added at 8 different concentrations with a concentration of solvent of 0.25% to avoid solvent toxicity. The plates were incubated at 37° C.+5% $CO_2$ for 48 h. The cells were then washed with 100 μL of HBSS and 150 μL of a 2% resazurin were added to the wells. The plates were again incubated at 37° C.+5% $CO_2$ for 1 h and their fluorescence was read using a Fluoroskan Ascent™ FL (thermo) using an excitation wavelength of 530 nm and an emission wavelength of 590 nm.

The $IC_{50}$ values obtained for the various extracts and fractions are reported in Table 8 below.

G is $R_2$ and E is

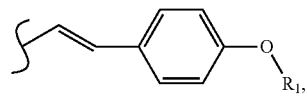

or

G and E are both single carbon atoms, said carbon atoms being directly linked together by a single bond, G being substituted by

and E being substituted by $R_6$;

TABLE 8

Antibiotic activity of *Populus balsamifera* bud ethanolic extract and of fractions thereof against *S. aureus* wild type strain (ATCC25923), *E. coli* (ATCC25922) and three strains of MRSAs (1, 2 and 3). $IC_{50}$ (along their standard error) and MIC values are shown. All values are in μg/ml.

| Extract/fractions | S. aureus WT | | E. Coli | | MRSA 1 | | MRSA 2 | | MRSA 3 | |
| --- | --- | --- | --- | --- | --- | --- | --- | --- | --- | --- |
| | $IC_{50}$ | MIC | $IC_{50}$ | MIC | $IC_{50}$ | MIC | $IC_{50}$ | MIC | $IC_{50}$ | MIC |
| Ethanolic extract | 1.6 ± 0.1 | 6.25 | >50 | >50 | 3.3 ± 0.1 | 6.25 | 3.5 ± 0.4 | 6.25 | 2.6 ± 0.3 | 12.5 |
| Methanol soluble fraction | 1.38 ± 0.09 | 6.25 | >50 | >50 | 2.5 ± 0.2 | 6.25 | 1.9 ± 0.1 | 6.25 | 2.1 ± 0.2 | 6.25 |
| Water soluble fraction | 5.6 ± 0.7 | | >200 | | | | | | | |
| Diethyl ether soluble fraction | 1.18 ± 0.06 | 3.12 | >50 | >50 | 2.0 ± 0.2 | 6.25 | 1.8 ± 0.2 | 6.25 | 2.4 ± 0.1 | 6.25 |
| Fraction A | 2.5 ± 0.3 | | >200 | | | | | | | |
| Fraction D | 2.1 ± 0.2 | | 83 ± 8 | | | | | | | |
| Fraction E | 0.78 ± 0.05 | 3.12 | >50 | >50 | 1.21 ± 0.09 | 3.12 | 0.87 ± 0.05 | 3.12 | 1.2 ± 0.1 | 3.12 |
| Fraction F | 3.2 ± 0.1 | 12.5 | >50 | >50 | 7.7 ± 0.4 | 25 | 3.0 ± 0.3 | 12.5 | 6.2 ± 0.7 | 25 |
| Fraction F4 | 0.87 ± 0.06 | 3.12 | >50 | >50 | 1.5 ± 0.1 | 3.12 | 0.96 ± 0.09 | 3.12 | 1.16 ± 0.09 | 3.12 |
| Fraction F5 | 6 ± 1 | | >200 | | | | | | | |
| Gentamycin | <0.005 | <0.005 | 0.009 ± 0.001 | 0.019 | <0.005 | <0.005 | <0.005 | <0.005 | 0.0060 ± 0.0004 | 0.019 |

The scope of the claims should not be limited by the preferred embodiments set forth in the examples, but should be given the broadest interpretation consistent with the description as a whole.

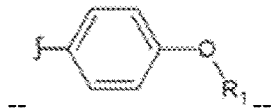

The invention claimed is:

1. A compound being an ethanolate, a methanolate or an ester of formula (I):

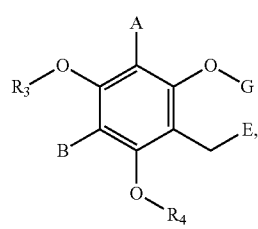

wherein:
one of A and B is H and the other is

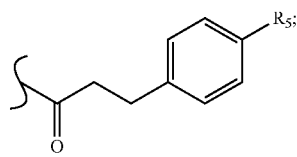

each of $R_1$, $R_2$, $R_3$, and $R_4$ independently being H or $C_1$-$C_{12}$ alkyl; and each of $R_5$ and $R_6$, independently being H, OH, $C_1$-$C_{12}$ alkyl, or $C_1$-$C_{12}$ alkoxy;

wherein said ester is obtained by esterification of an hydroxy group in formula I and is selected from:

(1) a methyl or ethyl carboxylic acid ester;

(2) a methyl or ethyl sulfonate ester;

(3) a methyl or ethyl phosphonate ester;

(4) a methyl or ethyl mono-, di- or triphosphate ester;

(5) a methyl or ethyl carbamic acid ester; or (6) a methyl or ethyl carbonic acid ester.

2. The compound of claim 1, being an ethanolate, a methanolate or ester of formula (1), (2) or (3):

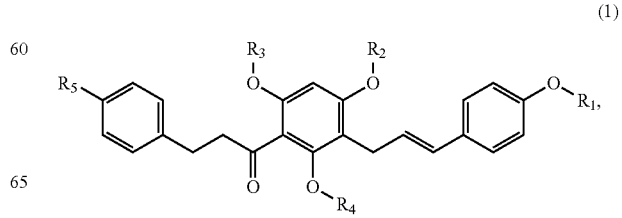

-continued (2)

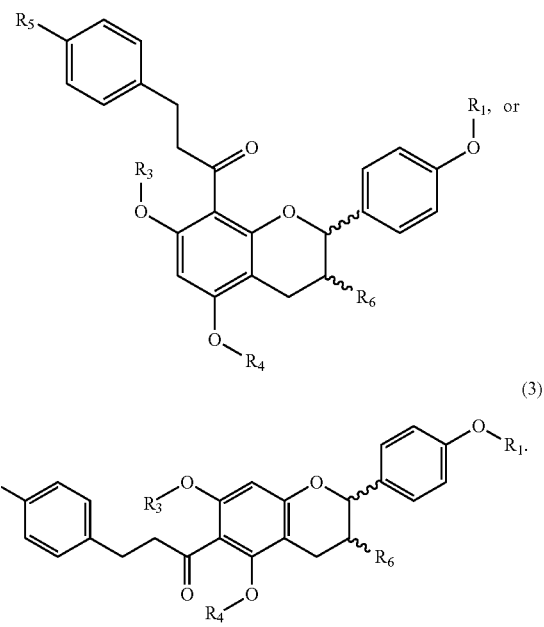

(3)

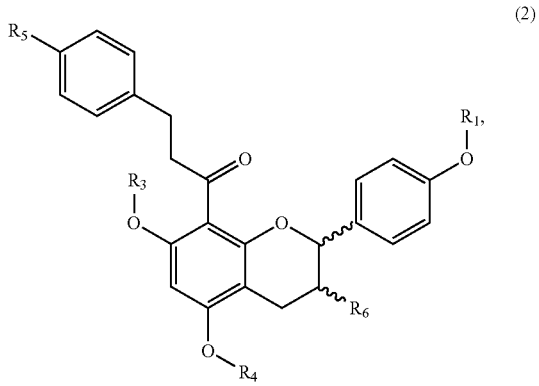

wherein said ester is obtained by esterification of an hydroxy group in formula (1), (2) or (3) and is selected from:

(1) a methyl or ethyl carboxylic acid ester;
(2) a methyl or ethyl sulfonate ester;
(3) a methyl or ethyl phosphonate ester;
(4) a methyl or ethyl mono-, di- or triphosphate ester;
(5) a methyl or ethyl carbamic acid ester; or
(6) a methyl or ethyl carbonic acid ester.

3. The compound of claim 1, wherein $R_1$ is H.
4. The compound of claim 1, wherein $R_2$ is H or $CH_3$.
5. The compound of claim 1, wherein $R_3$ is H.
6. The compound of claim 1, wherein $R_4$ is H or —$CH_3$.
7. The compound of claim 1, wherein $R_5$ is H, —OH or —O—$CH_3$.
8. The compound of claim 1, wherein $R_6$ is H or —OH.
9. A compound being an ethanolate, a methanolate or an ester:
(a) of formula (1):

(1)

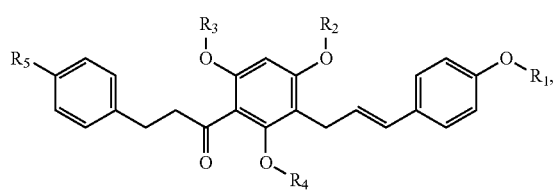

wherein:
(i) $R_1$, $R_3$ and $R_4$ are H, $R_2$ is $CH_3$ and $R_5$ is OH;
(ii) $R_1$, $R_2$, $R_3$ and $R_4$ are H, and $R_5$ is $OCH_3$; or
(iii) $R_1$, $R_2$, $R_3$, $R_4$ and $R_5$ are H, or
(b) of formula (2):

(2)

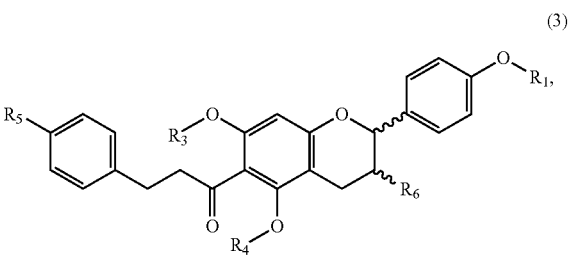

wherein:
(i) $R_1$, $R_3$, $R_4$, $R_5$ and $R_6$ are H and the stereochemistry of said compound is racemic;
(ii) $R_1$, $R_3$, $R_4$, $R_5$ and $R_6$ are H and the stereochemistry of said compound is 2S;
(iii) $R_1$, $R_3$, $R_4$, $R_5$ and $R_6$ are H and the stereochemistry of said compound is 2R;
(iv) $R_1$, $R_3$, $R_4$ and $R_6$ are H, $R_5$ is $OCH_3$ and the stereochemistry of said compound is racemic;
(v) $R_1$, $R_3$, $R_4$ and $R_6$ are H, $R_5$ is —O—$CH_3$ and the stereochemistry of said compound is 2S;
(vi) $R_1$, $R_3$, $R_4$ and $R_6$ are H, $R_5$ is —O—$CH_3$ and the stereochemistry of said compound is 2R;
(vii) $R_1$, $R_3$, and $R_6$ are H, $R_4$ is $CH_3$, $R_5$ is OH and the stereochemistry of said compound is racemic;
(viii) $R_1$, $R_3$, and $R_6$ are H, $R_4$ is $CH_3$, $R_5$ is OH and the stereochemistry of said compound is 2S;
(ix) $R_1$, $R_3$, and $R_6$ are H, $R_4$ is $CH_3$, $R_5$ is OH and the stereochemistry of said compound is 2R;
(x) $R_1$, $R_3$, $R_4$ and $R_5$ are H, $R_6$ is OH, and the stereochemistry of said compound is racemic;
(xi) $R_1$, $R_3$, $R_4$ and $R_5$ are H, $R_6$ is OH and the stereochemistry of said compound is 2S, 3S;
(xii) $R_1$, $R_3$, $R_4$ and $R_5$ are H, $R_6$ is OH and the stereochemistry of said compound is 2S, 3R;
(xiii) $R_1$, $R_3$ and $R_4$ are H, $R_5$ is —O—$CH_3$, $R_6$ is OH and the stereochemistry of said compound is racemic;
(xiv) $R_1$, $R_3$ and $R_4$ are H, $R_5$ is —O—$CH_3$, $R_6$ is OH and the stereochemistry of said compound is 2R, 3S; or
(xv) $R_1$, $R_3$ and $R_4$ are H, $R_5$ is —O—$CH_3$, $R_6$ is OH and the stereochemistry of said compound is 2S, 3R, or
(c) of formula (3):

(3)

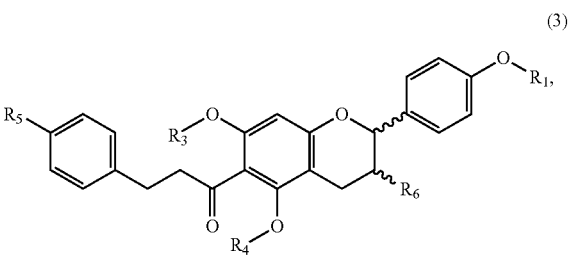

wherein:
(i) $R_1$, $R_3$, $R_4$, and $R_5$ are H, $R_6$ is OH and the stereochemistry of said compound is racemic;
(ii) $R_1$, $R_3$, $R_4$, and $R_5$ are H, $R_6$ is OH and the stereochemistry of said compound is 2R, 3S; or
(iii) $R_1$, $R_3$, $R_4$, and $R_5$ are H, $R_6$ is OH and the stereochemistry of said compound is 2S, 3R, and wherein said ester is obtained by esterification of an hydroxy group in formula (1), (2) or (3) and is selected from:
(1) a methyl or ethyl carboxylic acid ester;
(2) a methyl or ethyl sulfonate ester;
(3) a methyl or ethyl phosphonate ester;
(4) a methyl or ethyl mono-, di- or triphosphate ester;
(5) a methyl or ethyl carbamic acid ester; or
(6) a methyl or ethyl carbonic acid ester.

10. An alcoholic extract in liquid or dried form of a bud of a plant belonging to a species of *Populus*, the extract comprising at least one compound of:
(a) formula (I):

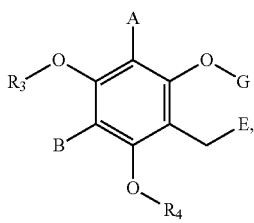

(I)

wherein:
one of A and B is H and the other is

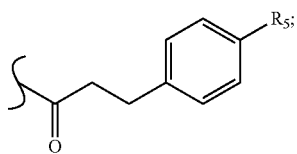

G is $R_2$ and E is

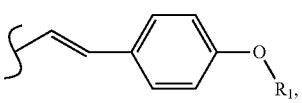

or
G and E are both single carbon atoms, said carbon atoms being directly linked together by a single bond, G being substituted by

and E being substituted by $R_6$;
each of $R_1$, $R_2$, $R_3$, and $R_4$ independently being H or $C_1$-$C_{12}$ alkyl; and
each of $R_5$ and $R_6$, independently being H, OH, $C_1$-$C_{12}$ alkyl, or $C_1$-$C_{12}$ alkoxy;

or
(b) formula (1):

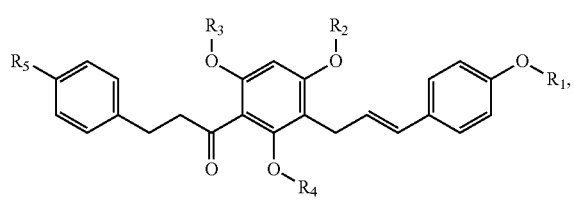

(1)

wherein:
(i) $R_1$, $R_3$ and $R_4$ are H, $R_2$ is $CH_3$ and $R_5$ is OH;
(ii) $R_1$, $R_2$, $R_3$ and $R_4$ are H, and $R_5$ is $OCH_3$; or
(iii) $R_1$, $R_2$, $R_3$, $R_4$ and $R_5$ are H;

or
(c) formula (2):

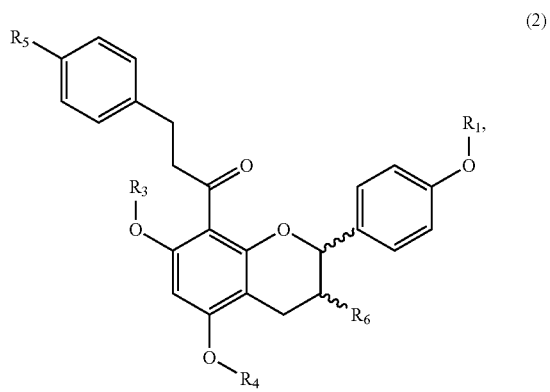

(2)

wherein:
(i) $R_1$, $R_3$, $R_4$, $R_5$ and $R_6$ are H and the stereochemistry of said compound is racemic;
(ii) $R_1$, $R_3$, $R_4$, $R_5$ and $R_6$ are H and the stereochemistry of said compound is 2S;
(iii) $R_1$, $R_3$, $R_4$, $R_5$ and $R_6$ are H and the stereochemistry of said compound is 2R;
(iv) $R_1$, $R_3$, $R_4$ and $R_6$ are H, $R_5$ is $OCH_3$ and the stereochemistry of said compound is racemic;
(v) $R_1$, $R_3$, $R_4$ and $R_6$ are H, $R_5$ is —O—$CH_3$ and the stereochemistry of said compound is 2S;
(vi) $R_1$, $R_3$, $R_4$ and $R_6$ are H, $R_5$ is —O—$CH_3$ and the stereochemistry of said compound is 2R;
(vii) $R_1$, $R_3$, and R are H, $R_4$ is $CH_3$, $R_5$ is OH and the stereochemistry of said compound is racemic;
(viii) $R_1$, $R_3$, and $R_6$ are H, $R_4$ is $CH_3$, $R_5$ is OH and the stereochemistry of said compound is 2S;
(ix) $R_1$, $R_3$, and $R_6$ are H, $R_4$ is $CH_3$, $R_5$ is OH and the stereochemistry of said compound is 2R;
(x) $R_1$, $R_3$, $R_4$ and $R_5$ are H, $R_6$ is OH, and the stereochemistry of said compound is racemic;
(xi) $R_1$, $R_3$, $R_4$ and $R_5$ are H, $R_6$ is OH and the stereochemistry of said compound is 2S, 3S;
(xii) $R_1$, $R_3$, $R_4$ and $R_5$ are H, $R_6$ is OH and the stereochemistry of said compound is 2S, 3R;
(xiii) $R_1$, $R_3$ and $R_4$ are H, $R_5$ is —O—$CH_3$, $R_6$ is OH and the stereochemistry of said compound is racemic;

(xiv) $R_1$, $R_3$ and $R_4$ are H, $R_5$ is —O—$CH_3$, $R_6$ is OH and the stereochemistry of said compound is 2R, 3S; or (xv) $R_1$, $R_3$ and $R_4$ are H, $R_5$ is —O—$CH_3$, $R_6$ is OH and the stereochemistry of said compound is 2S, 3R;

or (d) formula (3):

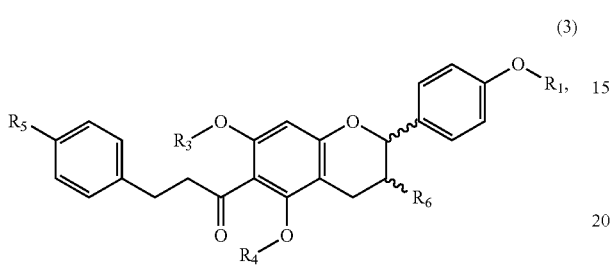

(3)

wherein:

(i) $R_1$, $R_3$, $R_4$, and $R_5$ are H, $R_6$ is OH and the stereochemistry of said compound is racemic;

(ii) $R_1$, $R_3$, $R_4$, and $R_5$ are H, $R_6$ is OH and the stereochemistry of said compound is 2R, 3S; or (iii) $R_1$, $R_3$, $R_4$, and $R_5$ are H, $R_6$ is OH and the stereochemistry of said compound is 2S, 3R.

11. The extract of claim 10, wherein the plant is *Populus balsamifera*.

12. The extract of claim 11, being an ethanolic extract, or a combination of several ethanolic extracts, in liquid form or dried form.

13. A methanolic extract of the dried ethanolic extract of claim 12, said methanolic extract fraction having optionally been extracted with hexane one or more times, said methanolic extract being in liquid or dried form.

14. A diethyl ether extract of the methanolic extract of claim 13, said diethyl ether extract having optionally been extracted with water one or more times, said diethyl ether extract being in liquid or dried form.

15. A fraction of the dried diethyl ether extract of claim 13.

16. A pharmaceutical composition comprising:

(i) a compound of:

(a) formula (I):

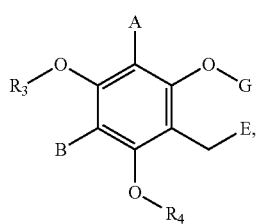

(I)

wherein:

one of A and B is H and the other is

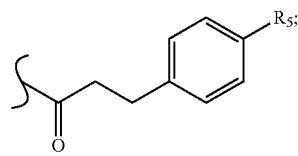

G is $R_2$ and E is

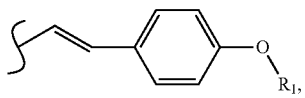

or

G and E are both single carbon atoms, said carbon atoms being directly linked together by a single bond, G being substituted by

and E being substituted by $R_6$;

each of $R_1$, $R_2$, $R_3$, and $R_4$ independently being H or $C_1$-$C_{12}$ alkyl; and each of $R_5$ and $R_6$, independently being H, OH, $C_1$-$C_{12}$ alkyl, or $C_1$-$C_{12}$ alkoxy;

or (b) formula (1):

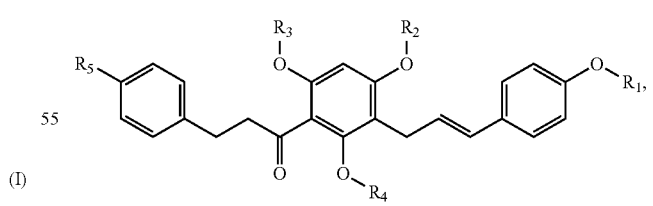

(1)

wherein:

(i) $R_1$, $R_3$ and $R_4$ are H, $R_2$ is $CH_3$ and $R_5$ is OH;

(ii) $R_1$, $R_2$, $R_3$ and $R_4$ are H, and $R_5$ is $OCH_3$; or (iii) $R_1$, $R_2$, $R_3$, $R_4$ and $R_5$ are H;

or
(c) formula (2):

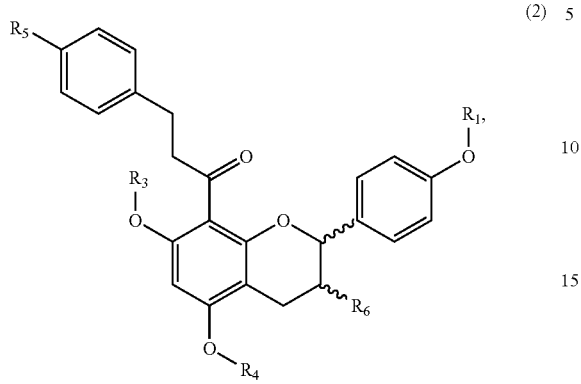

wherein:
(i) $R_1$, $R_3$, $R_4$, $R_5$ and $R_6$ are H and the stereochemistry of said compound is racemic;
(ii) $R_1$, $R_3$, $R_4$, $R_5$ and $R_6$ are H and the stereochemistry of said compound is 2S;
(iii) $R_1$, $R_3$, $R_4$, $R_5$ and $R_6$ are H and the stereochemistry of said compound is 2R;
(iv) $R_1$, $R_3$, $R_4$ and $R_6$ are H, $R_5$ is $OCH_3$ and the stereochemistry of said compound is racemic;
(v) $R_1$, $R_3$, $R_4$ and $R_6$ are H, $R_5$ is —O—$CH_3$ and the stereochemistry of said compound is 2S;
(vi) $R_1$, $R_3$, $R_4$ and $R_6$ are H, $R_5$ is —O—$CH_3$ and the stereochemistry of said compound is 2R;
(vii) $R_1$, $R_3$, and $R_6$ are H, $R_4$ is $CH_3$, $R_5$ is OH and the stereochemistry of said compound is racemic;
(viii) $R_1$, $R_3$, and $R_6$ are H, $R_4$ is $CH_3$, $R_5$ is OH and the stereochemistry of said compound is 2S;
(ix) $R_1$, $R_3$, and $R_6$ are H, $R_4$ is $CH_3$, $R_5$ is OH and the stereochemistry of said compound is 2R;
(x) $R_1$, $R_3$, $R_4$ and $R_5$ are H, $R_6$ is OH, and the stereochemistry of said compound is racemic;
(xi) $R_1$, $R_3$, $R_4$ and $R_5$ are H, $R_6$ is OH and the stereochemistry of said compound is 2S, 3S;
(xii) $R_1$, $R_3$, $R_4$ and $R_5$ are H, $R_6$ is OH and the stereochemistry of said compound is 2S, 3R;
(xiii) $R_1$, $R_3$ and $R_4$ are H, $R_5$ is —O—$CH_3$, $R_6$ is OH and the stereochemistry of said compound is racemic;
(xiv) $R_1$, $R_3$ and $R_4$ are H, $R_5$ is —O—$CH_3$, $R_6$ is OH and the stereochemistry of said compound is 2R, 3S; or
(xv) $R_1$, $R_3$ and $R_4$ are H, $R_5$ is —O—$CH_3$, $R_6$ is OH and the stereochemistry of said compound is 2S, 3R;
or
(d) formula (3):

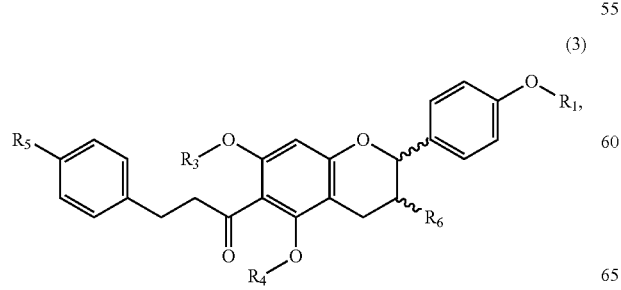

wherein:
(i) $R_1$, $R_3$, $R_4$, and $R_5$ are H, $R_6$ is OH and the stereochemistry of said compound is racemic;
(ii) $R_1$, $R_3$, $R_4$, and $R_5$ are H, $R_6$ is OH and the stereochemistry of said compound is 2R, 3S; or
(iii) $R_1$, $R_3$, $R_4$, and $R_5$ are H, $R_6$ is OH and the stereochemistry of said compound is 2S, 3R;
or (ii) a pharmaceutically acceptable salt, ester, methanolate or ethanolate of (i); or (iii) the extract of claim 10, or (iv) the fraction of (iii), wherein said composition further comprises a solubilizing agent, a wetting agent or an emulsifier, and
wherein said ester is obtained by esterification of an hydroxy group in formula I, (1), (2) or (3) and is selected from:
(1) a methyl or ethyl carboxylic acid ester;
(2) a methyl or ethyl sulfonate ester;
(3) a methyl or ethyl phosphonate ester;
(4) a methyl or ethyl mono-, di- or triphosphate ester;
(5) a methyl or ethyl carbamic acid ester; or
(6) a methyl or ethyl carbonic acid ester.

17. A method of treating a bacterial infection, the method comprising the step of administering an effective amount of:
(i) a compound of:
(a) formula (I):

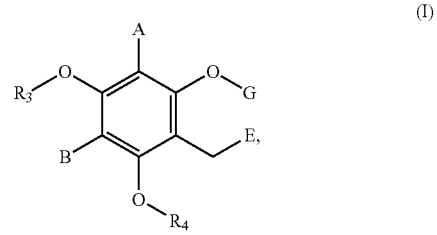

wherein:
one of A and B is H and the other is

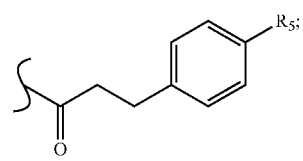

G is $R_2$ and E is

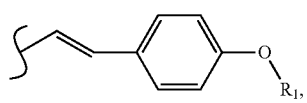

or
G and E are both single carbon atoms, said carbon atoms being directly linked together by a single bond, G being substituted by

and E being substituted by $R_6$;
  each of $R_1$, $R_2$, $R_3$, and $R_4$ independently being H or $C_1$-$C_{12}$ alkyl; and
  each of $R_5$ and $R_6$, independently being H, OH, $C_1$-$C_{12}$ alkyl, or $C_1$-$C_{12}$ alkoxy;
or
(ii) a pharmaceutically acceptable salt, ester, methanolate or ethanolate of (i), wherein said ester is obtained by esterification of an hydroxy group in formula I and is selected from:
  (1) a methyl or ethyl carboxylic acid ester;
  (2) a methyl or ethyl sulfonate ester;
  (3) a methyl or ethyl phosphonate ester;
  (4) a methyl or ethyl mono-, di- or triphosphate ester;
  (5) a methyl or ethyl carbamic acid ester; or
  (6) a methyl or ethyl carbonic acid ester; or
(iii) the extract of claim 10; or (iv) the fraction of (iii); or (v) any one of (i) to (iv) and a pharmaceutically acceptable carrier, to a subject in need thereof.

18. The method of claim 17, wherein the subject is a human.

19. The method of claim 17, wherein the subject is a non-human animal.

20. The method of claim 17, wherein said compound of is of formula (1), (2) or (3):

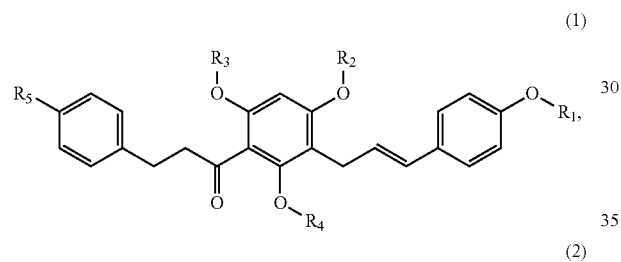

(1)

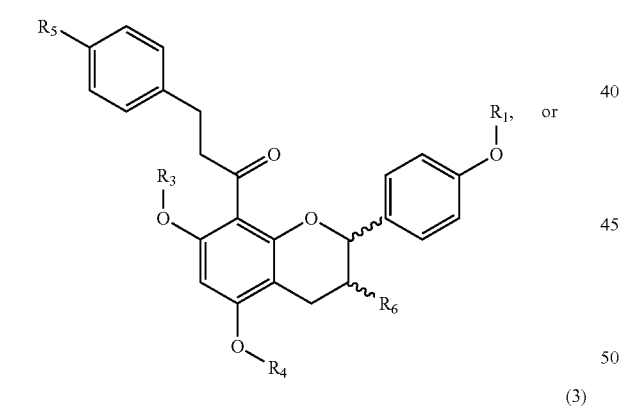

(2)

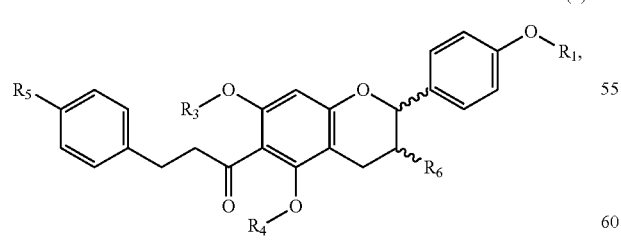

(3)

wherein $R_1$, $R_2$, $R_3$, $R_4$, $R_5$ and $R_6$ are as defined in claim 17.

21. The method of claim 17, wherein $R_1$ is H.
22. The method of claim 17, wherein $R_2$ is H or $CH_3$.
23. The method of claim 17, wherein $R_3$ is H.
24. The method of claim 17, wherein $R_4$ is H or —$CH_3$.
25. The method of claim 17, wherein $R_5$ is H, —OH or —O—$CH_3$.
26. The method of claim 17, wherein $R_6$ is H or —OH.
27. The method of claim 17, wherein said compound is of:
(a) formula (1):

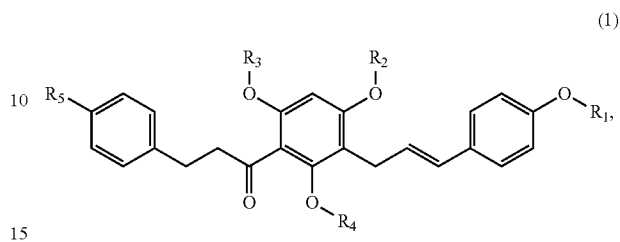

(1)

wherein:
  (i) $R_1$, $R_3$ and $R_4$ are H, $R_2$ is $CH_3$ and $R_5$ is OH;
  (ii) $R_1$, $R_2$, $R_3$ and $R_4$ are H, and $R_5$ is $OCH_3$; or
  (iii) $R_1$, $R_2$, $R_3$, $R_4$ and $R_5$ are H;
or
(b) formula (2):

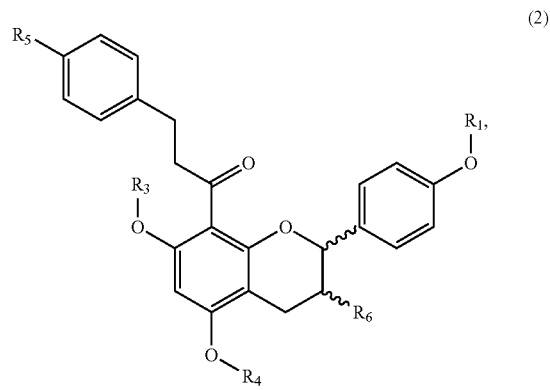

(2)

wherein:
  (i) $R_1$, $R_3$, $R_4$, $R_5$ and $R_6$ are H and the stereochemistry of said compound is racemic;
  (ii) $R_1$, $R_3$, $R_4$, $R_5$ and $R_6$ are H and the stereochemistry of said compound is 2S;
  (iii) $R_1$, $R_3$, $R_4$, $R_5$ and $R_6$ are H and the stereochemistry of said compound is 2R;
  (iv) $R_1$, $R_3$, $R_4$ and $R_6$ are H, $R_5$ is $OCH_3$ and the stereochemistry of said compound is racemic;
  (v) $R_1$, $R_3$, $R_4$ and $R_6$ are H, $R_5$ is —O—$CH_3$ and the stereochemistry of said compound is 2S;
  (vi) $R_1$, $R_3$, $R_4$ and $R_6$ are H, $R_5$ is —O—$CH_3$ and the stereochemistry of said compound is 2R;
  (vii) $R_1$, $R_3$, and $R_6$ are H, $R_4$ is $CH_3$, $R_5$ is OH and the stereochemistry of said compound is racemic;
  (viii) $R_1$, $R_3$, and $R_6$ are H, $R_4$ is $CH_3$, $R_5$ is OH and the stereochemistry of said compound is 2S;
  (ix) $R_1$, $R_3$, and $R_6$ are H, $R_4$ is $CH_3$, $R_5$ is OH and the stereochemistry of said compound is 2R;
  (x) $R_1$, $R_3$, $R_4$ and $R_5$ are H, $R_6$ is OH, and the stereochemistry of said compound is racemic;
  (xi) $R_1$, $R_3$, $R_4$ and $R_5$ are H, $R_6$ is OH and the stereochemistry of said compound is 2S, 3S;
  (xii) $R_1$, $R_3$, $R_4$ and $R_5$ are H, $R_6$ is OH and the stereochemistry of said compound is 2S, 3R;
  (xiii) $R_1$, $R_3$ and $R_4$ are H, $R_5$ is —O—$CH_3$, $R_6$ is OH and the stereochemistry of said compound is racemic;

(xiv) $R_1$, $R_3$ and $R_4$ are H, $R_5$ is —O—$CH_3$, $R_6$ is OH and the stereochemistry of said compound is 2R, 3S; or (xv) $R_1$, $R_3$ and $R_4$ are H, $R_5$ is —O—$CH_3$, $R_6$ is OH and the stereochemistry of said compound is 2S, 3R; or (c) formula (3):

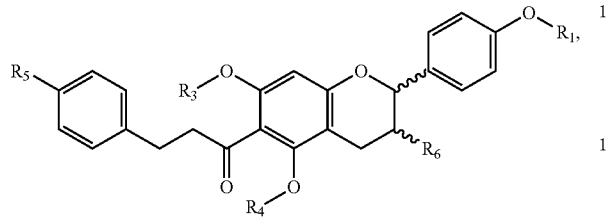

(3)

wherein:

(i) $R_1$, $R_3$, $R_4$, and $R_5$ are H, $R_6$ is OH and the stereochemistry of said compound is racemic;

(ii) $R_1$, $R_3$, $R_4$, and $R_5$ are H, $R_6$ is OH and the stereochemistry of said compound is 2R, 3S; or (iii) $R_1$, $R_3$, $R_4$, and $R_5$ are H, $R_6$ is OH and the stereochemistry of said compound is 2S, 3R.

28. The extract of claim 10, wherein said extract is a $C_1$-$C_{10}$ aliphatic alcohol extract.

29. The extract of claim 10, wherein said extract has antibiotic activity against *Staphylococcus Aureus* wild type strain and Methicillin Resistant *Staphylococcus Aureus* (MRSA) strain.

* * * * *

UNITED STATES PATENT AND TRADEMARK OFFICE
CERTIFICATE OF CORRECTION

PATENT NO. : 9,499,509 B2  
APPLICATION NO. : 14/425147  
DATED : November 22, 2016  
INVENTOR(S) : Pichette et al.

Page 1 of 2

It is certified that error appears in the above-identified patent and that said Letters Patent is hereby corrected as shown below:

In the Claims

In Claim 1, the definitions of G and E are missing and should appear at the very end of Column 33, Line 65 as follows:

-- G is $R_2$ and E is 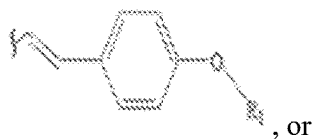 , or

G and E are both single carbon atoms, said carbon atoms being directly linked together by a single bond, G being substituted by 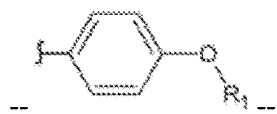 and E being substituted by $R_6$; --

In Claim 10, Line 60, the chemical formula is missing a bond between the oxygen and the phenyl and should appear as follows:

-- 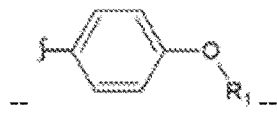 --

In Claim 16, Line 30, the chemical formula is missing a bond between the oxygen and the phenyl and should appear as follows:

-- 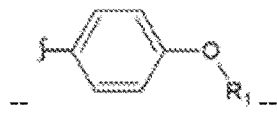 --

Signed and Sealed this  
Thirty-first Day of January, 2023

*Katherine Kelly Vidal*

Katherine Kelly Vidal  
*Director of the United States Patent and Trademark Office*

CERTIFICATE OF CORRECTION (continued)
U.S. Pat. No. 9,499,509 B2

In Claim 17, Line 65, the chemical formula is missing a bond between the oxygen and the phenyl and should appear as follows: